US011633146B2

United States Patent

Leng et al.

(10) Patent No.: US 11,633,146 B2
(45) Date of Patent: Apr. 25, 2023

(54) AUTOMATED CO-REGISTRATION OF PROSTATE MRI DATA

(71) Applicant: Regents of the University of Minnesota, Minneapolis, MN (US)

(72) Inventors: Ethan Yize Leng, Minneapolis, MN (US); David Henry Porter, Plymouth, MN (US); Gregory John Metzger, Lake Elmo, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 457 days.

(21) Appl. No.: 16/734,139

(22) Filed: Jan. 3, 2020

(65) Prior Publication Data

US 2020/0214619 A1 Jul. 9, 2020

Related U.S. Application Data

(60) Provisional application No. 62/788,230, filed on Jan. 4, 2019.

(51) Int. Cl.
*G01V 3/00* (2006.01)
*A61B 5/00* (2006.01)
(Continued)

(52) U.S. Cl.
CPC ............ *A61B 5/4381* (2013.01); *A61B 5/055* (2013.01); *A61B 5/7275* (2013.01);
(Continued)

(58) Field of Classification Search
USPC .......................................................... 600/423
See application file for complete search history.

(56) References Cited

U.S. PATENT DOCUMENTS 5,800,353 A 9/1998 McLaurin, Jr.
6,004,267 A 12/1999 Tewari et al.
(Continued)

FOREIGN PATENT DOCUMENTS

CN 103699904 A 4/2014
CN 104794426 A 7/2015
(Continued)

OTHER PUBLICATIONS

Allam et al., "Interobserver Variability in the Diagnosis of High-Grade Prostatic Intraepithelial Neoplasia and Adenocarcinoma," Modern Pathology, vol. 9, No. 7, Jul. 1996, 10 pp.
(Continued)

*Primary Examiner* — Walter L Lindsay, Jr.
*Assistant Examiner* — Frederick Wenderoth
(74) *Attorney, Agent, or Firm* — Shumaker & Sieffert, P.A.

(57) ABSTRACT

Medical imaging analysis systems are configured to perform automatic image registration algorithms that perform three-dimensional (3D), affine, and/or intensity-based co-registration of magnetic resonance imaging (MRI) data, such as multiparametric MRI (mpMRT) data, using mutual information (MI) as a similarity metric. An apparatus comprises a computer-readable storage medium storing a plurality of imaging series of magnetic resonance imaging (MRI) data for imaged tissue of a patient; and a processor coupled to the computer-readable storage medium. The processor is configured to receive the imaging series of MRI data; identify a volume of interest (VOI) of each image of the imaging series of MRI data; compute registration parameters for the
(Continued)

HISTOPATHOLOGY DATA 24
8
MEDICAL IMAGING ANALYSIS SYSTEM 10
MRI MODALITY 13
DATA REGISTRATION MODULE 27
IMAGE INTERPRETATION MODULE 12
MODEL GENERATION MODULE 22
MEDICAL IMAGING DATA 18
REGISTERED MEDICAL IMAGING DATA 19
DISPLAY 11
VISUALIZATION 20
VISUALIZATION GENERATION MODULE 14
MULTIPARAMETRIC CANCER MODEL 16

VOIs through the maximization of mutual information of the corrected VOIs; and register the VOIs using the computed registration parameters.

29 Claims, 6 Drawing Sheets

(51) Int. Cl.

| | |
|---|---|
| ***G06T 3/00*** | (2006.01) |
| ***G06T 7/00*** | (2017.01) |
| ***G06T 7/62*** | (2017.01) |
| ***G16H 50/20*** | (2018.01) |
| ***G16H 30/20*** | (2018.01) |
| ***G01R 33/565*** | (2006.01) |
| ***G01R 33/56*** | (2006.01) |
| ***A61B 5/055*** | (2006.01) |

(52) U.S. Cl.
CPC ..... *G01R 33/5608* (2013.01); *G01R 33/5659* (2013.01); *G06T 3/0075* (2013.01); *G06T 7/0012* (2013.01); *G06T 7/62* (2017.01); *G16H 30/20* (2018.01); *G16H 50/20* (2018.01); *G06T 2207/10088* (2013.01); *G06T 2207/30081* (2013.01); *G06T 2207/30096* (2013.01)

(56) References Cited

U.S. PATENT DOCUMENTS

| | | | |
|---|---|---|---|
| 7,245,748 B2 | 7/2007 | Degani et al. | |
| 7,831,293 B2 | 11/2010 | Ellis et al. | |
| 8,295,575 B2 | 10/2012 | Feldman et al. | |
| 8,386,012 B2 | 2/2013 | Fehre et al. | |
| 8,518,650 B2 | 8/2013 | Mitchell et al. | |
| 8,548,562 B2 | 10/2013 | Trachtenberg et al. | |
| 8,718,350 B2 | 5/2014 | Metzger et al. | |
| 9,858,665 B2 | 1/2018 | Metzger et al. | |
| 2005/0186642 A1 | 8/2005 | Tacha | |
| 2007/0232882 A1* | 10/2007 | Glossop | A61B 17/3211 600/407 |
| 2008/0214950 A1 | 9/2008 | Fehre et al. | |
| 2010/0169024 A1 | 7/2010 | Madabhushi et al. | |
| 2010/0329529 A1 | 12/2010 | Feldman et al. | |
| 2012/0257811 A1 | 10/2012 | Metzger et al. | |
| 2013/0064439 A1* | 3/2013 | Khurd | G06T 7/194 382/131 |
| 2013/0196868 A1 | 8/2013 | Lebowitz et al. | |
| 2013/0287283 A1 | 10/2013 | Kamath et al. | |
| 2014/0073907 A1 | 3/2014 | Kumar et al. | |
| 2014/0185891 A1 | 7/2014 | Schoenmeyer et al. | |
| 2014/0303041 A1 | 10/2014 | Hayes et al. | |
| 2015/0201910 A1* | 7/2015 | Zhao | A61B 8/5261 600/440 |
| 2015/0301054 A1 | 10/2015 | Liao et al. | |
| 2015/0317431 A1 | 11/2015 | Gronberg et al. | |
| 2016/0292855 A1* | 10/2016 | Metzger | G06T 7/0012 |
| 2017/0261584 A1* | 9/2017 | James | A61B 5/055 |
| 2018/0156883 A1* | 6/2018 | Öz | G06T 7/11 |
| 2018/0182099 A1 | 6/2018 | Lesniak | |
| 2020/0211189 A1 | 7/2020 | Yip et al. | |
| 2020/0226462 A1 | 7/2020 | Maddison et al. | |
| 2020/0250817 A1 | 8/2020 | Leng et al. | |
| 2020/0372235 A1 | 11/2020 | Peng | |
| 2020/0394825 A1 | 12/2020 | Stumpe | |
| 2021/0150701 A1 | 5/2021 | Thagaard et al. | |
| 2021/0201485 A1 | 7/2021 | Chukka et al. | |
| 2022/0058839 A1 | 2/2022 | Chang et al. | |

FOREIGN PATENT DOCUMENTS

| | | | |
|---|---|---|---|
| CN | 105184798 A | 12/2015 | |
| CN | 103593843 B * | 4/2016 | |
| CN | 106204561 A | 12/2016 | |
| CN | 106778005 A | 5/2017 | |
| CN | 107133638 B | 1/2020 | |
| EP | 2545527 B1 * | 7/2014 | G06T 7/0012 |

OTHER PUBLICATIONS

Anderson et al., "Multiparametric MRI identifies and stratifies prostate cancer lesions: Implications for targeting intraprostatic targets," Brachytherapy, vol. 13, No. 3, Jan. 2014, 7 pp.
Araujo et al., "Classification of breast cancer histology images using Convolutional Neural Networks," PLoS One, vol. 12, No. 6, Jun. 2017, 14 pp.
Arevalo et al., "An unsupervised feature learning framework for basal cell carcinoma image analysis," Artificial Intelligence in Medicine, vol. 64, No. 2, Jun. 2015, 15 pp.
Barentsz et al., "ESUR prostate MR guidelines 2012," Eur Radiol, Feb. 10, 2012, 12 pp.
Brockman et al., "Nomogram Predicting Prostate Cancer-specific Mortality for Men with Biochemical Recurrence After Radical Prostatectomy," European Urology, vol. 67, No. 6, Jun. 2015, 17 pp.
Chan et al., "Detection of prostate cancer by integration of line-scan diffusion, T2-mapping and T2-weighted magnetic resonance imaging; a multichannel statistical classifier," Med. Phys., vol. 30, No. 9, Sep. 2003, 9 pp.
Chappelow et al., "Elastic registration of multimodal prostate MRI and histology via multiattribute combined mutual information," Medical Physics—The International Journal of Medical Physics Research and Practice, vol. 38, No. 4, Apr. 2011, 14 pp.
Chappelow et al., "Improving supervised classification accuracy using non-rigid multimodal image registration: detecting prostate cancer," Proceedings of SPIE, vol. 6915, Mar. 2018, 12 pp.
Cheung et al., "Using manual prostate contours to enhance deformable registration of endorectal MRI," Computer Methods and Programs in Biomedicine, vol. 108, No. 1, Oct. 2012, 8 pp.
Cruz-Roa et al., "Accurate and Reproducible Invasive Breast Cancer Detection in Whole-Slide Images: A Deep Learning Approach for Quantifying Tumor Extent," Scientific Reports, vol. 7, Article No. 46450, Apr. 2017, 14 pp.
Dabir et al., "Comparative Analysis of three- and two-antibody Cocktails to AMACR and Basal Cell Markers for the Immunohistochemical Diagnosis of Prostate Carcinoma," Diagnostic Pathology, vol. 7, Article No. 81, Jul. 2012, 6 pp.
Delongchamps et al., "Multiparametric magnetic resonance imaging for the detection and localization of prostate cancer: combination of T2-weighted, dynamic contrast-enhanced and diffusion-weighted imaging," BJU International, vol. 107, No. 9, May 2011, 8 pp.
DeLuca et al., "A Fully Automatic Method to Register the Prostate Gland on T2-weighted and EPI-DWI Images," 2011 Annual International Conference of the IEEE Engineering in Medicine and Biology Society, Aug. 2011, 4 pp.
Dickinson et al., "Magnetic Resonance Imaging for the Detection, Localisation, and Characterisation of Prostate Cancer: Recommendations from a European Consensus Meeting," European Urology, vol. 59, Dec. 21, 2010, 18 pp.
Divrik et al., "Increasing the number of biopsies increases the concordance of Gleason scores of needle biopsies and prostatectomy specimens," Urologic Oncology: Seminars and Original Investigations, vol. 25, No. 5, Sep.-Oct. 2007, 7 pp.
Efron et al., "An Introduction to the Bootstrap," CRC Press, 1998, 11 pp. (Applicant points out, in accordance with MPEP 609.04(a), that the year of publication, 1998, is sufficiently earlier than the effective U.S. filing date, so that the particular month of publication is not in issue.).
Eichelberger et al., "Predicting Tumor Volume in radical Prostatectomy Specimens From Patients With Prostate Cancer," Am J Clin Pathol, vol. 120, No. 3, Sep. 2003, 6 pp.
Epstein et al., "A Contemporary Prostate Cancer Grading System: A Validated Alternative to the Gleason Score," European Urology, vol. 69, No. 3, Mar. 2016, 19 pp.

(56) References Cited

OTHER PUBLICATIONS

Friedman et al., "Regularization Paths for Generalized Linear Models via Coordinate Descent," Journal of Statistical Software, vol. 33, No. 1, Jan. 2010, 22 pp.
Garcia-Reyes et al., "Detection of prostate cancer with multiparametric MRI (mpMRI): effect of dedicated reader education on accuracy and confidence of index and anterior cancer diagnosis," Abdom Imagine, vol. 41, No. 1, Jan. 2015, 20 pp.
Ghosh et al., "A Genetic Algorithm-Based Level Set Curve Evolution for Prostate Segmentation on Pelvic CT and MRI Images," Chapter 6 in Biomedical Image Analysis and Machine Learning, Technologies: Applications and Techniques, 2010, 25 pp. (Applicant points out, in accordance with MPEP 609.04(a), that the year of publication, 2010, is sufficiently earlier than the effective U.S. filing date, so that the particular month of publication is not in issue.).
Giannini et al., "A fully automatic computer aided diagnosis system for peripheral zone prostate cancer detection using multi-parametric magnetic resonance imaging," Computerized Medical Imaging and Graphics, vol. 46, Dec. 2015, 8 pp.
Giannini et al., "A prostate CAD system based on multiparametric analysis of DCE T1-w, and DW automatically registered images," Proceedings of SPIE—The International Society for Optical Engineering, vol. 8670, Feb. 2013, 7 pp.
Gibbs et al., "Comparison of Quantitative T2 Mapping and Diffusion-Weighted Imagine in the Normal and Pathologic Prostate," vol. 46, No. 6, Dec. 2001, 5 pp.
Glass et al., "SIMPLE: A Sequential Immunoperoxidase Labeling and Erasing Method," Journal of Histochemistry and Cytochemistry, vol. 57, No. 10, Oct. 2009, 7 pp.
Guo et al., "Intraductal Carcinoma of the Prostate on Needle Biopsy: Histologic Features and Clinical Significance," Modern Pathology: An Official Journal of the United States and Canadian Academy of Pathology, Inc., vol. 19, No. 12, Dec. 2006, 8 pp.
Gurcan et al., "Histopathological Image Analysis: A Review," IEEE Reviews in Biomedical Engineering, vol. 2, Oct. 2009, 25 pp.
Hao et al., "Nonrigid Registration of Prostate Diffusion-Weighted MRI," Journal of Healthcare Engineering, vol. 2017, Article ID 9296354, Jun. 2017, 12 pp.
Hedgire et al., "Multiparametric magnetic resonance imaging of prostate cancer," Indian J Radiol Imaging, vol. 22, No. 3, Jul.-Sep. 2012, 24 pp.
Heidenreich et al., "EAU Guidelines on Prostate Cancer. Part 1: Screening, Diagnosis, and Local Treatment With Curative Intent—Update 2013," European Urology, vol. 65, No. 1, Jan. 2014, 14 pp.
Herawi et al., "Immunohistochemical Antibody Cocktail Staining (p63/HMWCK/AMACR) of Ductal Adenocarcinoma and Gleason Pattern 4 Cribriform and Noncribriform Acinar Adenocarcinomas of the Prostate," The American Journal of Surgical Pathology, vol. 31, No. 6, Jun. 2007, 6 pp.
Homer et al., "Driven-Equilibrium Single-Pulse Observation of T1 Relaxation/ A Reevaluation of a Rapid "New," Method for Determining NMR Spin-Lattice Relaxation Times," Journal of Magnetic Resonance, vol. 63, No. 2, Jun. 15, 1985, 11 pp.
Humphrey, P.A., "Diagnosis of adenocarcinoma in prostate needle biopsy tissue," Journal of Clinical Pathology, vol. 60, No. 1, Jan. 2007, 8 pp.
Jin et al., "Detection of Prostate Cancer with Multiparametric MRI Utilizing the Anatomic Structure of the Prostate," Statistics in Medicine, vol. 37, No. 22, Sep. 2018, 28 pp.
Kalavagunta et al., "Analysis of Quantitative MRI and Pathology based on Co-registered Regions of Prostate Cancer," Proc. Intl. Soc. Mag. Reson. Med., vol. 20, 2012, 1 pp. (Applicant points out, in accordance with MPEP 609.04(a), that the year of publication, 2012, is sufficiently earlier than the effective U.S. filing date, so that the particular month of publication is not in issue.).
Kalavagunta et al., "Registration of In Vivo Prostate MRI and Pseudo-Whole Mount Histology Using Local Affine Transformations Guided by Internal Structures (LATIS)," Journal of Magnetic Resonance Imaging: JMRI, vol. 41, No. 4, Apr. 2015, 11 pp.
Kalavagunta, "Multiparametric MRI and Digital Pathology of Prostate Cancer, An Image Registration based Correlation Study," Nov. 2013; Donald Gleason Conference on Prostate and Urologic Cancers University of Minnesota, Department of Radiology, 1 pp.
Kalvagunta et al., "Pixel-Wise Multi-parametric Assessment of Prostate Cancer from Co-registered regions of Pathologically defined Disease," Proc. Intl. Soc. Mag. Reson. Med., vol. 22, 2014, 1 pp. (Applicant points out, in accordance with MPEP 609.04(a), that the year of publication, 2014, is sufficiently earlier than the effective U.S. filing date, so that the particular month of publication is not in issue.).
Kather et al., "Multi-class texture analysis in colorectal cancer histology," Scientific Reports, vol. 6, Article 27988, Jun. 2016, 11 pp.
Khosravi et al., "Deep Convolutional Neural Networks Enable Discrimination of Heterogeneous Digital Pathology Images," E. Bio Medicine, vol. 27, Jan. 2018, 12 pp.
Kim et al., "Localization of Prostate Cancer Using 3T MRI, Comparison of T2-Weighted and Dynamic Contrast-Enhanced Imaging," J Comput Assist Tomogr, vol. 30, No. 1, Jan.-Feb. 2006, 5 pp.
Kothari et al., "Removing Batch Effects From Histopathological Images for Enhanced Cancer Diagnosis," IEEE Journal of Biomedical and Health Informatics, vol. 18, No. 3, May 2014, 23 pp.
Krajewska et al., "Image Analysis Algorithms for Immunohistochemical Assessment of Cell Death Events and Fibrosis in Tissue Sections," Journal of Histochemistry and Cytochemistry, vol. 57, No. 7, Jul. 2009, 15 pp.
Kuefer et al., "Methylacyl-CoA Racemase: Expression Levels of this Novel Cancer Biomarker Depend on Tumor Differentiation," The American Journal of Pathology, Vo. 161, No. 3, Sep. 2002, 8 pp.
Kurhanewicz et al., "Multiparametric magnetic resonance imaging in prostate cancer: present and future," Curr Opin Urol, vol. 18, No. 1, Jan. 2008, 7 pp.
Kwak et al., "Automated prostate cancer detection using T2-weighted and high-b-value diffusion-weighted magnetic resonance imaging," Medical Physics—The International Journal of Medical Physics Research and Practice, vol. 42, No. 5, May 2015, 11 pp.
Langer et al., "Prostate Cancer Detection With Multi-parametric MRI: Logistic Regression Analysis of Quantitative T2, Diffusion-Weighted Imaging, and Dynamic Contrast-Enhanced MRI," Journal of Magnetic Resonance Imaging, vol. 30, No. 2, Aug. 2009, 8 pp.
Lavasani et al., "Automatic Prostate Cancer Segmentation Using Kinetic Analysis in Dynamic Contrast-Enhanced MRI," Journal of Biomedical & Physics Engineering, vol. 8, No. 1, Mar. 2018, 10 pp.
Le Bihan et al., "Separation of Diffusion and Perfusion in Intravoxel Incoherent Motion MR Imaging," Radiology, vol. 168, No. 2, Aug. 1988, 9 pp.
Lemaitre et al., "Computer-Aided Detection and diagnosis for prostate cancer based on mono and multiparametric MRI: a Review," Computers in Biology and Medicine, vol. 60, May 2015, 24 pp.
Leng et al., "Estimation of prostate cancer distribution on pathology slides via image analysis of IHC-stained slides," Abstract presented at the International Society for Magnetic Resonance in Medicine (ISMRM) 2018 conference, accepted Feb. 2, 2018 and presented Jun. 9, 2018, 3 pp.
Leng et al., "Colorimetric Image Analysis of H&E and IHC Slides for Automated Pathologic Annotation of Prostate Cancer," ISMRM Workshop on Advanced in Multiscale Cancer Detection: From Micro to Macro, Dublin, Ireland, 2018, 1 pp. (Applicant points out, in accordance with MPEO 609.04(a), that the year of publication, 2018, is sufficiently earlier than the effective U.S. filing date, so that the particular month of publication is not in issue.).
Li et al., "Improved noninvasive prostate cancer assessment using multiparametric magnetic resonance imaging," 2016 IEEE 13th International Symposium on Biomedical Imaging (ISBI), Apr. 2016, 5 pp.
Liney et al., "Comparison of Conventional Single Echo and Multi-Echo Sequences with a Fast Spin-Echo Sequence for Quantitative T2 Mapping: Application to the Prostate," JMRI, Jul. 1996, 5 pp.
Liney et al., "In Vivo Quantification of Citrate Concentration and Water T2 Relaxation Time of the Pathologic Prostate Gland using 1H MRS and MRI," Magnetic Resonance Imaging, vol. 15, No. 10, Jul. 20, 1997, 10 pp.

(56) References Cited

OTHER PUBLICATIONS

Litjens et al., "Computer-Aided Detection of Prostate Cancer in MRI," IEEE Transactions on Medical Imaging, vol. 33, No. 5, May 2014, 10 pp.
Litjens et al., "Deep Learning as a Tool for Increased Accuracy and Efficiency of Histopathological Diagnosis," Scientific Reports, vol. 6, Article No. 26286, May 2016, 11 pp.
Lotan et al., "Cytoplasmic PTEN Protein Loss Distinguishes Intraductal Carcinoma of the Prostate from High-Grade Prostatic Intraepithelial Neoplasia," Modern Pathology, vol. 26, No. 4, Apr. 2013, 17 pp.
Lughezzani et al., "Multicenter European External Validation of a Prostate Health Index-based Nomogram for Predicting Prostate Cancer at Extended Biopsy," European Urology, vol. 66, No. 5, Nov. 2014, 7 pp.
Luo et al., "alpha-Methylacyl-CoA Racemase: A New Molecular Marker for Prostate Cancer," Cancer Research, vol. 62, No. 8, Apr. 2002, 7 pp.
Macenko et al., "A method for normalizing histology slides for quantitative analysis," In IEEE International Symposium on Biomedical Imaging: From Nano to Macro, Jun. 2009, 4 pp.
Makni et al., "Combining a deformable model and a probabilistic framework for an automatic 3D segmentation of prostate on MRI," International Journal of Computer Assisted Radiology and Surgery, vol. 4, No. 181, Dec. 2008, 8 pp.
Marin et al., "Prostate cancer: Computer-Aided Diagnosis on Multiparametric MRI," Proceedings in SPIE, vol. 10572, Nov. 2017, 7 pp.
Martin et al., "Automated Segmentation of the Prostate in 3D MR images Using a Probabilistic Atlas and a Spatially Constrained Deformable Model," Medical Physics—The International Journal of Medical Physics Research and Practice, vol. 37, No. 4, Mar. 2010, 21 pp.
Malulewicz et al., "Anatomic segmentation improves prostate cancer detection with artificial neural networks analysis of 1H MRSI," J Magn Reson Imaging, vol. 40, No. 6, Dec. 2014, 18 pp.
McNeal et al., "Capsular Penetration in Prostate Cancer. Significance for Natural History and Treatment," The American Journal of Surgical Pathology, vol. 14, No. 3, Mar. 1990, 8 pp.
Metzger et al., "Detection find grading of prostate cancer using model-based spectral fitting," Proc. Intl. Soc. Mag. Reson. Med., vol. 22, 2014, 1 pp. (Applicant points out, in accordance with MPEP 609.04(a), that the year of publication, 2014, is sufficiently earlier than the effective U.S. filing date, so that the particular month of publication is not in issue.).
Metzger et al., "Detection of Prostate Cancer: Quantitative Multiparametric MR Imaging Models Developed Using Registered Correlative Histopathology," Radiology, vol. 279, No. 3, Jun. 2016, 12 pp.
Metzger et al., "Development of Multigene Expression Signature Maps at the Protein level from Digitized Immunohistochemistry Slides," PLos ONE, vol. 7, No. 3, Mar. 2012, 12 pp.
Montironi et al., "Gleason grading of prostate cancer in needle biopsies or radical prostatectomy specimens: contemporary approach, current clinical significance and sources of pathology discrepancies," BJU International, vol. 95, No. 8, Jun. 2005, 7 pp.
Montironi et al., "Prostatic Intraepithelial Neoplasia: Its Morphological and Molecular Diagnosis and Clinical Significance," BJU International, vol. 108, Nov. 2011, 6 pp.
Morton et al., "Screening Mammograms: Interpretation with Computer-aided Detection—Prospective Evaluation," Radiology, vol. 239, No. 2, May 2006, 9 pp.
Mullerad et al., "Prostate Cancer: Detection of Extracapsular Extension by Genitourinary and General Body Radiologists at MR Imaging," vol. 232, No. 1, Jul. 2004, 7 pp.
Nam et al., "JPStitch 2.0: a Software for Volumetric Reconstruction and Analysis of Digitized Pathology," University of Minnesota, Nov. 2013; Donald Gleason Conference on Prostate and Urologic Cancers; Minneapolis, MN, 1 pp.
Ng et al., "Is Triple Immunostaining with 34betaE12, p63, find Racemase in Prostate Cancer Advantageous? A Tissue Microarray Study," American Journal of Clinical Pathology, vol. 127, No. 2, Feb. 2007, 6 pp.
Niaf et al., "Computer-aided diagnosis of prostate cancer in the peripheral zone using multiparametric MRI," Physics in Medicine and Biology, vol. 57, No. 23, Jun. 21, 2012, 19 pp.
Orczyk et al., "Imaging of prostate cancer: a platform for 3D co-registration of in-vivo MRI ex-vivo MRI and pathology," Proc SPIE, Feb. 23, 2012, 18 pp.
Orczyk et al., "Preliminary Experience With a Novel Method of Three-Dimensional Co-Registration of Prostate Cancer Digital Histology and in Vivo Multiparametric MRI," Clinical Radiology, vol. 68, No. 12, Aug. 2013, 12 pp.
Parker et al., "Experimentally-Derived Functional Form for a Population-Averaged High-Temporal-Resolution Arterial Input Function for Dynamic Contrast-Enhanced MRI," Magnetic Resonance in Medicine, vol. 56, No. 5, Nov. 2006, 8 pp.
Pedregosa et al., "Scikit-learn: Machine Learning in Python," Journal of Machine Learning Research, vol. 12, No. 85, Oct. 2011, 6 pp.
Puech et al., "Computer-assisted diagnosis of prostate cancer using DCE-MRI data: design, implementation and preliminary results," Int J Cars, vol. 4, Oct. 21, 2008, 10 pp.
Rizzardi et al., "Elevated HA and HMMR are Associated with Biochemical Failure in Patients with Intermediate Grade Prostate Tumors," Cancer, vol. 120, No. 12, Jun. 2014, 10 pp.
Rizzardi et al., "Evaluation of Protein Biomarkers of Prostate Cancer Aggressiveness," BMC Cancer, vol. 14, Article No. 244, Apr. 2014, 14 pp.
Rizzardi et al., "Quantitative Comparison of Immunohistochemical Staining Measured by Digital Image Analysis Versus Pathologist Visual Scoring," Diagnostic Pathology, vol. 7, Article No. 42, Jun. 2012, 10 pp.
Rosenkrantz et al., "Prostate Cancer Localization Using Multiparametric MR Imagine: Comparison of Prostate Imaging Reporting and Data System (PI-RADS) and Likert Scales," Radiology, vol. 269, No. 2, Nov. 2013, 11 pp.
Rubin et al., "alpha-Methylacyl Coenzyme A Racemase as a Tissue Biomarker for Prostate Cancer," Jama, vol. 287, No. 13, Apr. 2002, 9 pp.
Ruprecht et al., "MRI of the prostate: Interobserver agreement compared with histopathologic outcome after radical prostatectomy," European Journal of Radiology, vol. 81, Dec. 28, 2010, 5 pp.
Sanda et al., "Quality of Life find Satisfaction with Outcome among Prostate-Cancer Survivors," The New England Journal of Medicine, vol. 358, No. 12, Mar. 20, 2008, 12 pp.
Shah et al., "Atypical Cribriform Lesions of the Prostate: Clinical Significance, Differential Diagnosis and Current Concept of Intraductal Carcinoma of the Prostate," Advances in Anatomic Pathology, vol. 19, No. 4, Jul. 2012, 9 pp.
Shah et al., "Decision Support System for Localizing Prostate Cancer Based on Multiparametric Magnetic Resonance Imaging," Medical Physics, The International Journal of Medical Physics Research and Practice, vol. 39, No. 7, Jun. 2002, 11 pp.
Sharma et al., "Deep convolutional neural networks for automatic classification of gastric carcinoma using whole slide images in digital histopathology," Computerized Medical Imaging and Graphics: The Official journal of the Computerized Medical Imaging Society, vol. 61, Nov. 2017, 12 pp.
Siegel et al., "Cancer Statistics, 2017," CA Cancer Journal for Clinicians, vol. 67, No. 1, Jan./Feb. 2017, 24 pp.
Signoretti et al., "p63 is a prostate basal cell marker and is required for prostate development," The American Journal of Pathology, vol. 157, vol. 6, Dec. 2000, 7 pp.
Sobecki et al., "Feature Extraction Optimized for Prostate Lesion Classification," ICBBT '17: Proceedings of the 9th International Conference on Bioinformatics and Biomedical Technology, May 2017, 6 pp.
Stember et al., "Pilot Study of a Novel Tool for Input-Free Automated Identification of Transition Zone Prostate Tumors using T2- and Diffusion-Weighted Signal and Textural Features," Journal of Magnetic Resonance Imaging, vol. 40, No. 2, Aug. 2014, 5 pp.

(56) References Cited

OTHER PUBLICATIONS

Stephenson et al., "Postoperative Nomogram Predicting the 10-Year Probability of Prostate Cancer Recurrence After Radical Prostatectomy," Journal of Clinical Oncology: Official Journal of the American Society of Clinical Oncology, vol. 23, vol. 28, Oct. 2005, 8 pp.

Swindle et al., "Do margins matter? The prognostic significance of positive surgical margins in radical prostatectomy specimens," The Journal of Urology, vol. 179, May 2008, 5 pp.

Thoeny et al., "Diffusion-Weighted Imaging of the Parotid Gland: Influence of the Choice of b-Values on the Apparent Diffusion Coefficient Value," Journal of Magnetic Resonance Imaging, vol. 20, No. 5, Nov. 2004, 5 pp.

Tiwari et al., "Multimodal Wavelet Embedding Representation for data Combination (MaWERiC): Integrating Magnetic Resonance Imaging and Spectroscopy for Prostate Cancer Detection," NMR Biomed, vol. 25, No. 4, Apr. 2012, 30 pp.

Tofts et al., "Modeling Tracer Kinetics in Dynamic Gd-DTPA MR Imaging," JMRI, vol. 7, No. 1, Jan.-Feb. 1997, 11 pp.

Van der Loos et al., "Multiple Immunoenzyme Staining: Methods and Visualizations for the Observation with Spectral Imaging," Journal of Histochemistry and Cytochemistry, vol. 56, No. 4, Apr. 2008, 16 pp.

Viswanath et al., "Central Gland and Peripheral Zone Prostate Tumors Have Significantly Different Quantitative Imaging Signatures on 3 Tesla Endorectal, In Vivo T2-Weighted MR Imagery," Journal of Magnetic Resonance Imaging, vol. 36, No. 1, Jul. 2012, 12 pp.

Viswanath et al., "Integrating structural and functional imaging for computer assisted detection of prostate cancer on multi-protocol in vivo 3 Tesla MRI," Proceedings of SPIE—The International Society for Optical Engineering, vol. 7260, Feb. 2009, 21 pp.

Vos et al., "Automatic computer-aided detection of prostate cancer based on multiparametric magnetic resonance image analysis," Physics in Medicine and Biology, vol. 57, Mar. 6, 2012, 16 pp.

Vos et al., "Computer-assisted Analysis of Peripheral Zone Prostate Lesions Using T2-weighted and Dynamic Contrast Enhanced T1-weighted MRI," Physics in Medicine and Biology, vol. 55, No. 6, Mar. 2010, 16 pp.

Vos et al., Combining T2-weighted with dynamic MR images for computerized classification of prostate lesions, Proceedings of SPIE—The International Society for Optical Engineering, vol. 6915, Article No. 69150W, Mar. 2008, 8 pp.

Wang et al., "Searching for prostate cancer by fully automated magnetic resonance imaging classification: deep learning versus non-deep learning," Scientific Reports, vol. 7, Article # 15415, Nov. 2017, 8 pp.

Wei et al., "Comprehensive Comparison of Health-Related Quality of Life After Contemporary Therapies for Localized Prostate Cancer," Journal of Clinical Oncology, vol. 20, No. 2, Jan. 15, 2002, 10 pp.

Wibmer et al., "Haralick Texture Analysis of Prostate MRI: Utility for Differentiating Non-cancerous Prostate from Prostate Cancer and Differentiating Prostate Cancers with Different Gleason Scores," European Radiology, vol. 25, No. 10, Oct. 2015, 21 pp.

Wilt, "The Prostate Cancer Intervention Versus Observation Trial:VA/NCI/AHRQ Cooperative Studies Program #407 (PIVOT): Design and Baseline Results of a Randomized Controlled Trial Comparing Radical Prostatectomy With Watchful Waiting for Men With Clinically Localized Prostate Cancer," Journal of the National Cancer Institute Monographs, vol. 45, Dec. 2012, 7 pp.

Wojno et al., "The Utility of Basal Cell-Specific Anti-Cytokeratin Antibody (34βE12) in the Diagnosis of Prostate Cancer. A Review of 228 Cases," The American Journal of Surgical Pathology, vol. 19, No. 3, Mar. 1995, 10 pp.

Xiao et al., "Determining histology-MRI slice correspondences for defining MRI-based disease signatures of prostate cancer," Computerized Medical Imaging and Graphics, vol. 35, No. 7-8, Oct.-Dec. 2011, 11 pp.

Yamada et al., "Efficacy of Distortion Correction on Diffusion Imaging: Comparison of FSL Eddy and Eddy Correct Using 30 and 60 Directions Diffusion Encoding," PLoS One, vol. 9, No. 11, Nov. 2014, 9 pp.

Zhao et al., Anatomical Feature-Guided Mutual Information Registration of Multimodal Prostate MRI. In Yoshida H., Sakas G., Linguraru M.G. (eds) Abdominal Imaging. Computational and Clinical Applications. ABD-MICCAI 2011, Lecture Notes in Computer Science, vol. 7029. Springer, Berlin, Heidelberg Sep. 2012, 8 pp.

"Computer-aided diagnosis," Wikipedia, accessed from https://en.wikipedia.org/wiki/Computer-aided_diagnosis, on May 27, 2020, 17 pp.

"Immunohistochemistry," Wikipedia, accessed from indirect method of IHC staining on May 28, 2020, 9 pp.

"Pattern recognition," Wikipedia, accessed from https://en.wikipedia.org/wiki/Pattern_recognition on May 27, 2020, 11 pp.

Prosecution History from U.S. Appl. No. 15/089,273, dated Oct. 10, 2017 through Oct. 10, 2017, 15 pp.

Giannini et al., "A Novel and Fully Automated Registration Method for Prostate Cancer Detection Using Multiparametric Magnetic Resonance Imaging," Journal of Medical Imaging and Health Informatics, vol. 5, No. 6, Nov. 2015, 12 pp.

* cited by examiner

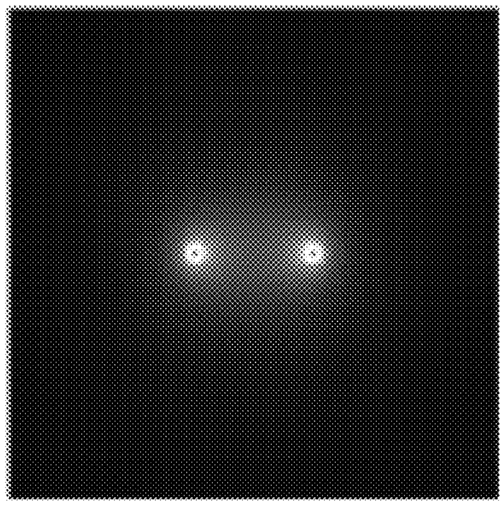
FIG. 3A
FIG. 3B
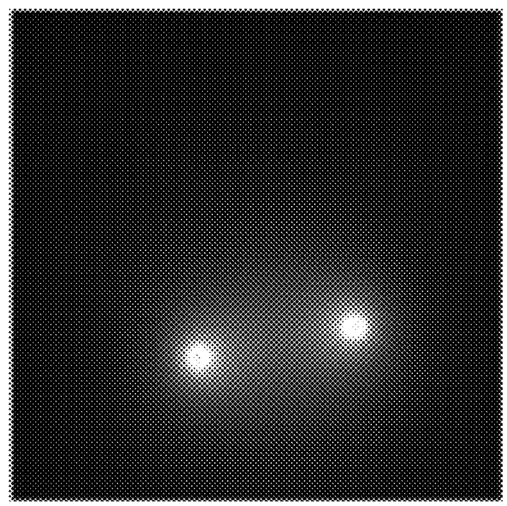
FIG. 3C
FIG. 3D

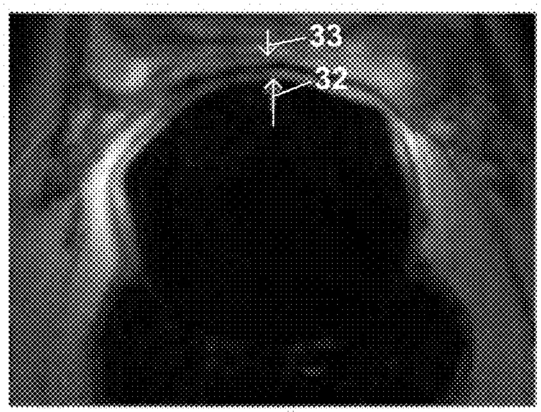
FIG. 4A
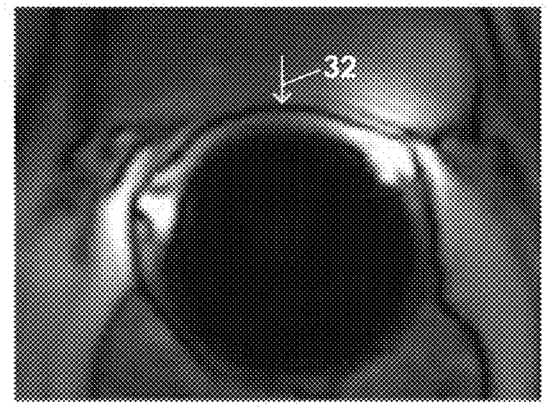
FIG. 4B
32
FIG. 4C
32
FIG. 4D

AUTOMATED CO-REGISTRATION OF PROSTATE MRI DATA

This application claims the benefit of U.S. Provisional Patent Application No. 62/788,230 filed Jan. 4, 2019, the entire content being incorporated herein by reference.

STATEMENT REGARDING FEDERALLY SPONSORED RESEARCH OR DEVELOPMENT

This invention was made with government support under T32-GM008244, R01-CA155268, and P41-EB015894 awarded by the National Institutes of Health and W81XWH-15-1-0477 awarded by the Department of Defense. The government has certain rights in the invention.

BACKGROUND

There is much interest in computer aided diagnosis (CAD) systems that apply computational models to aid the diagnosis of patients.

SUMMARY

In general, this disclosure describes automatic image registration systems that perform three-dimensional (3D), affine, and/or intensity-based co-registration of magnetic resonance imaging (MRI) data, such as multiparametric MRI (mpMRI) data, from a plurality of imaging sessions using mutual information (MI) and genetic algorithms. MRI data from multiple imaging series co-registered according to the techniques described herein can be used for development and prospective application of models for computer-aided diagnosis (CAD) systems that perform automated or semi-automated analysis of MRI data.

As one example, multiparametric magnetic resonance imaging (mpMRI), which is a combination of anatomic and functional MRI techniques, is a useful clinical tool in the detection and diagnosis of prostate cancer. However, interpretation of mpMRI data is difficult and time-consuming, and highly-dependent on observer experience. Computer-aided diagnosis (CAD) systems for prostate cancer are described that are beneficial for accurate and quick diagnosis. However, due to patient motion during the course of a study, as well as distortions inherent to imaging methods, the mpMRI data may be misaligned, which may result in limited accuracy in the ability of the CAD systems to accurately predict prostate cancer. Systems are described herein that provide technical solutions to the technical problem of potentially misaligned MRI data (e.g., mpMRI data). For example, the systems described herein can improve accurate analysis of mpMRI data through the spatial co-localization of the prostate anatomy in plurality (e.g., including all) of the acquired image series.

In some examples, the techniques of this disclosure may be executed in three parts (phases). A first part may include the definition of a volume of interest (VOI) on which registration parameters may be optimized. The VOI may be obtained from automated or manual segmentation of the prostate capsule. A second part may include corrections for the presence of an endorectal coil (ERC). An ERC is a hardware element used for signal reception in prostate MRI that also introduces distortions that may confound registration.

In image registration problems, one set of images is termed the target series, and all other sets of images are termed the source series. One goal of image registration algorithms implemented by the systems described herein is to spatially transform the source series (e.g., all of the source series) so that the source series are aligned with the target series. Procedurally, a system may identify the target and source imaging series before performing the registration process itself. A third part may include solution of the registration problem, which involves designating one imaging series from the mpMRI data as the target series and designating all others as the source series, then determining the best registration parameters via maximization of mutual information (MI) between the target series and each of the source series.

The techniques of this disclosure may be performed through the execution of software code implementing an algorithm that performs image registration for prostate mpMRI data sets. The algorithm incorporates methods that improve registration accuracy and robustness.

In some example implementations, the medical imaging analysis system may be configured to co-register MRI data as described herein and further analyze the co-registered MRI data to render predictive prostate cancer visualizations using, for example, quantitative multiparametric magnetic resonance imaging (mpMRI) models developed using co-registered correlative histopathology. The disclosure provides techniques for the development and usage of mpMRI models for user-independent detection and visualization of prostate cancer (PCa).

In one example, a method includes receiving, by a computing device, an imaging series of multiparametric magnetic resonance imaging (mpMRI) data, identifying, by the computing device, a volume of interest (VOI) of each image of the imaging series of mpMRI data, correcting, by the computing device, distortions that affect the intensity values in each of the VOIs, optimizing registration parameters, by the computing device, for the corrected VOIs through the maximization of mutual information of the corrected VOIs, and registering, by the computing device, the VOIs using the computed registration parameters.

In another example, a method comprises receiving, by a computing device, multiple imaging series of magnetic resonance imaging (mpMRI) data for imaged tissue of a patient and identifying, by the computing device either manually or automatically, a volume of interest (VOI) of each image of the imaging series of mpMRI data. The method further comprises computing, by the computing device, registration parameters for the corrected VOIs through the maximization of mutual information of the corrected VOIs and registering, by the computing device, the VOIs using the computed registration parameters.

In another example, an apparatus comprises a computer-readable storage medium storing an image series of mpMRI data. A processor coupled to the computer-readable storage medium is configured to receive the imaging series of mpMRI data, identify a VOI of each image of the imaging series of mpMRI data, correct distortions that affect the intensity values in each of the VOIs, calculate the optimal registration parameters for the corrected VOIs through the maximization of mutual information of the corrected VOIs, and carry out the registration of the VOIs using the computed registration parameters.

In another example, an apparatus comprises a computer-readable storage medium storing a plurality of imaging series of magnetic resonance imaging (MRI) data for imaged tissue of a patient; and a processor coupled to the computer-readable storage medium. The processor is configured to receive the imaging series of MRI data; identify a volume of interest (VOI) of each image of the imaging series of MRI data; compute registration parameters for the VOIs through the maximization of mutual information of the corrected VOIs; and register the VOIs using the computed registration parameters.

In another example, an apparatus comprises means for receiving an imaging series of mpMRI data, means for identifying a VOI of each image of the imaging series of mpMRI data, means for correcting distortions that affect the intensity values in each of the VOIs, means for optimizing registration parameters for the corrected VOIs through the maximization of mutual information of the corrected VOIs, and means for registering the VOIs using the computed registration parameters.

In another example, this disclosure describes a computer-readable storage medium storing instructions that, when executed, cause one or more processors to receive an imaging series of mpMRI data, identify a VOI of each image of the imaging series of mpMRI data, correct distortions that affect the intensity values in each of the VOIs, calculate the optimal registration parameters for the corrected VOIs through the maximization of mutual information of the corrected VOIs, and carry out the registration of the VOIs using the computed registration parameters.

In each of the above examples, the registered VOIs may then be used to detect the presence of cancer (e.g., in a prostate).

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 3A-3D are images illustrating intensity correction for the ERC sensitivity profile.

FIGS. 4A-4D are images demonstrating the AP translation component for registration of DCE data.

DETAILED DESCRIPTION

Figure 1:
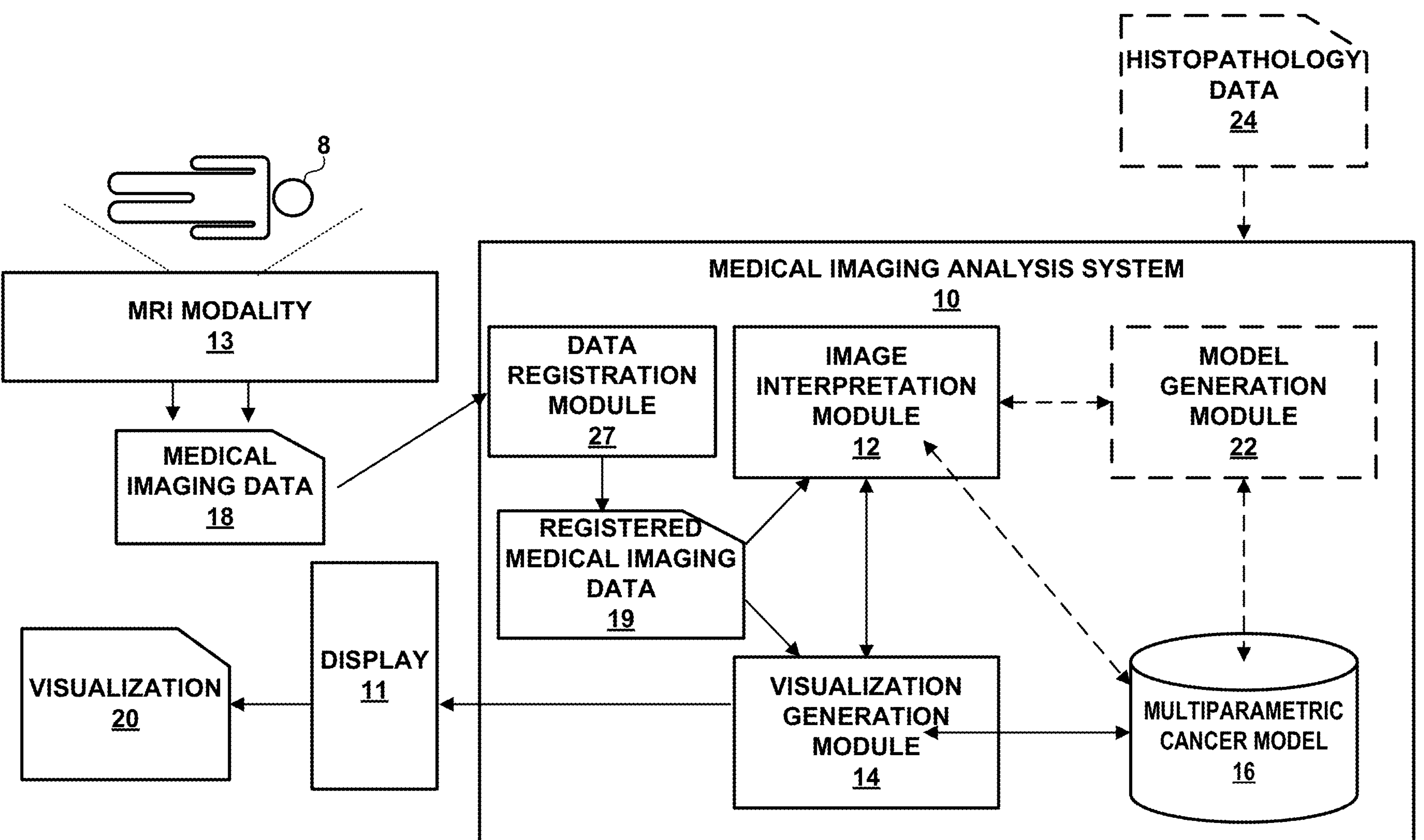
FIG. 1 is a block diagram illustrating an example medical imaging analysis system configured in accordance with one or more techniques of the present disclosure.

FIG. 1 is a block diagram illustrating an example medical imaging analysis system 10 ("system 10") in accordance with one or more techniques of the present disclosure. In the example of FIG. 1, system 10 may represent a system in which medial image data analysis for computer-aided diagnosis is integrated within medical imaging device, such as a magnetic resonance imaging (MRI) system, having a Multiparametric magnetic resonance imaging (mpMRI) input modality 13 for producing medical imaging data 18 and/or receiving the medical imaging data from other devices. In other examples, system 10 may be a computer-aided design (CAD) system or a computing device or computing system, such as a mobile computing device (e.g., a smartphone, a tablet computer, a personal digital assistant, and the like), a desktop computing device, a server system, a distributed computing system (e.g., a "cloud" computing system), or any other device capable of receiving medical imaging data 18 and performing the techniques described herein. As described herein, the spatial co-localization of the prostate anatomy in all of the acquired image series through 3D, affine, and/or intensity-based co-registration of mpMRI data using mutual information (MI) as the similarity metric improves the accurate analysis of MRI data 18 from patient 8 by system 10. System 10 then automatically constructs and/or applies multiparametric medical imaging models and/or computationally applies such models to the registered (aligned) mpMRI data 19 for patient 8 to generate predictive prostate cancer visualizations for use in medical diagnosis, medical research, medical testing, or other fields. In accordance with the techniques described herein, system 10 may receive as input, medical imaging data, such as medical imaging data 18, process medical imaging data 18 to align the data for patient 8 collected over an imaging session, and provide one or more visualizations (e.g., results 20) that indicate predicted cancer.

As shown in the example of FIG. 1, system 10 includes image interpretation module 12, visualization generation module 14, and multiparametric cancer model 16. In some examples, system 10 may also include database model generation module 22. Each of modules 12, 14, and 22 may be hardware, firmware, software, or some combination thereof. When implemented in software, modules 12, 14, and 22 comprises software instructions that execute on one or more programmable processors of system 10. Model 16 may, in the example of FIG. 1, represent a data repository or other collection of information that is accessible and/or modifiable by one or more of modules 12, 14, and 22 and stored on a computer-readable storage medium (e.g., disk or memory) of system 10.

In the example of FIG. 1, data registration module 27 is configured to receive and process medical imaging data 18, which typically takes the form of magnetic resonance imaging (MRI) data or, in some examples, multiparametric magnetic resonance imaging (mpMRI) data. Medical imaging data 18, in various examples, may be data that represents one or more images of tissue of patient 8 over one or more scanning sessions. That is, medical imaging data 18 may be generated by a medical imaging device, such as a magnetic resonance imaging (MRI) machine, when the medical imaging device scans tissue of patient 8. As one example, medical imaging data 18 may represent various two-dimensional (2D) images of a prostate gland of patient 8. Each 2D image may be a different plane of the scanned tissue. That is, the medical imaging device that generates medical imaging data 18 may take multiple 2D scans, each at a different point along a third dimension. In this way, the composite of medical imaging data 18 may, in some examples, be a series of planes (e.g., "slices") of the scanned tissue.

As described herein, data registration module 27 of medical imaging analysis system 10 executes semi-automatic or automatic image registration algorithms that performs 3D, affine, intensity-based co-registration of multiparametric magnetic resonance imaging (mpMRI) data using mutual information (MI) as the similarity metric. As further described, in some examples, the algorithms may be configured to implement:

1. Automated or manual determination of the volume of interest (VOI) on which registration parameters are optimized. The VOI may, in some examples, be determined from radiologists' annotation of the prostate capsule.
2. Automated correction for the presence of the instruments such as endorectal coil, which a hardware element commonly used for signal reception in prostate MRI that also introduces distortions that may confound registration.
3. Optimization in which the best registration parameters are computed via maximization of MI between imaging series. In some examples, as further explained below, the registration parameters that are optimized by data registration module 27 are entries of a transformation matrix (e.g., a 4×4 matrix) that represents the mapping for each pixel within images of the source series for transformation to the target series. Thus, in this example, data registration module 27 computes the optimal registration parameters by computing the optimal affine transform. In some examples, data registration module 27 computes the transformation matrix as the product of other component transformation matrices, each of which represents a single affine operation (either translation, scaling, shearing, or rotation). In examples, data registration module 27 executes the optimization using a genetic algorithm, rather than gradient descent or quasi-Newton methods, to compute the global optimum solution for the registration parameters in terms of maximization of MI, which enables better registration results on average.

Image interpretation module 12 receives registered medical imaging data 19 and may determine one or more 2D parameter maps corresponding to the imaged tissue. A 2D parameter map may indicate the value of a parameter at each location of the scanned tissue. For instance, image interpretation module 12 may generate a parameter map for one or more of an apparent T2 (T2) parameter, an apparent diffusion coefficient (ADC) parameter, pharmacokinetic parameters $K^{Trans}$, $k_{ep}$, and/or an area under the gadolinium concentration time curve over 90 s (AUGC90) parameter. In other words, image interpretation module 12 may process medical imaging data 18 to determine multiparametric mappings of the imaged tissue. Image interpretation module 12 may send the parameter mappings to one or more other components of analysis system 10, such as to visualization generation module 14.

Visualization generation module 14 is operable to analyze parameter maps received from image interpretation module 12 by applying one or more multiparametric cancer models 16. Based on the analysis of the parameter maps, visualization generation module 14 generates information indicating whether the imaged tissue has predicted cancer. That is, visualization generation module 14 applies multiparametric cancer model 16 to predict, based on registered medical imaging data 19, whether various regions of the tissue of patient 8 includes cancerous tissue and, based on the analysis, produce a graphical visualization illustrating the prediction. As one example, visualization generation module 14 may create an overlay image for registered medical imaging data 19 that shows and identifies regions of the imaged tissue that are predicted to be cancer. The overlay may, in some examples, visually depict areas of the tissue (as shown in medical imaging data 18) that are predicted to be cancer based on multiparametric cancer model 16.

Visualization generation module 14, in the example of FIG. 1, generates and outputs for display visualization 20, including at least an indication of the predicted cancer. Visualization 20 may, in some examples, be a 2D or 3D graphical representation of the imaged tissue, with visual indications of cancer regions (e.g., cancer lesions). In some examples, visualization 20 may be output for display, such as at a display device 11 operatively coupled to analysis system 10. In other examples, visualization 20 may be output to one or more other devices for further processing, storage, and/or display.

In some examples, system 10 may include model generation module 22. Model generation module 22 of system 10 may use medical imaging training data (e.g., received from imaged interpretation module 12) and corresponding histopathology data 24 to generate multiparametric cancer model 16. That is, model generation module 22 may receive medical imaging training data from image interpretation module 12 and may receive histopathology data 24. Histopathology data 24 may be annotated, digitized images of the tissue(s) shown in the received medical imaging training data. For instance, histopathology data 24 may be created by excising or removing the imaged tissue, fixing the tissue, and sectioning the tissue. The sectioned tissue may be digitized and annotated to indicate regions of the tissue that actually are cancer. Model generation module 22 may use the digitized and annotated histopathology data to determine characteristics of medical imaging data that corresponds to actual cancer. In order to do so, model generation module 22 may register the histopathology data to the medical imaging training data so that a specific location in a digitized image from histopathology data 24 corresponds (at least substantially) to the same actual location as the specific location in an image of the medical imaging training data. That is, model generation module may modify or otherwise adjust histopathology data 24 to "fit" the corresponding medical imaging training data. Methods for registering the histopathology data are further described herein.

Using the registered histopathology data 24 and medical imaging training data, model generation module 22 may generate a predictive cancer model and store the model as multiparametric cancer model 16. In some examples, the model may represent an equation that, when applied to values of parameters in registered medical imaging data 19, results in a score (e.g., a Composite Biomarker Score or CBS) that indicates whether or not the corresponding tissue is likely to be cancer. For instance, model 16 may, in some examples, be a set of coefficients for respective parameters and/or threshold CBS values. For each value of the parameter maps for imaged tissue, the parameter values may be plugged into the equation, and the resulting CBS value may be evaluated against the threshold CBS values. If the threshold values are satisfied, analysis system 10 may indicate that the corresponding tissue is likely cancer.

In one example, analysis system 10 may be used to generate a multiparametric cancer model using medical imaging data and co-registered histopathology data, and/or use the multiparametric model to provide at least one indication of whether or not imaged tissue likely includes cancer. As such, medical imaging analysis system 10 may be configured to render predictive prostate cancer visualizations using quantitative multiparametric magnetic resonance imaging (mpMRI) models developed using co-registered correlative histopathology. For example, the co-registered MRI data may be utilized for developing and using mpMRI models for user-independent, voxel-wise detection and visualization of prostate cancer (PCa) utilizing co-registered correlative histopathology as the ground truth. In one example, A processor coupled to the computer-readable storage medium is configured execute registration module 27 to produce registered medical imaging data 19 by executing an automatic image registration algorithm that performs three-dimensional (3D), affine, and/or intensity-based co-registration of mpMRI data using mutual information (MI) as the similarity metric. The processor may then execute visualization generation module 14 to apply multiparametric model 16 to the first parametric map and the second parametric map to generate at least one Composite Biomarker Score (CBS) for the imaged tissue of the patient. The multiparametric model 16 specifies a multiparametric operation based on at least the first parameter and the second parameter that is based on co-registered histopathology data and respective sets of medical imaging training data. In one example, the multiparametric model 16 specifies a multiparametric operation based on at least the first parameter and the second parameter that is based on models developed from separate data consisting of co-registered histopathology data and respective sets of medical imaging training data. The processor is further configured to generate and output, based on the respective CBS for each voxel of the imaged tissue, a visual indication of whether the corresponding imaged tissue is predicted to include cancer. The indication may, for example, comprise an overlay image for the medical imaging data for the imaged tissue, the overlay including regions of the predicted cancer. Example techniques for predicted prostate cancer visualization using quantitative mpMRI models developed using co-registered correlative histopathology are described in U.S. Pat. No. 9,858,665 (application Ser. No. 15/089,273), entitled "Medical imaging device rendering predictive prostate cancer visualizations using quantitative multiparametric MRI models," issued on Jan. 1, 2018, the entire content of which is incorporated by reference herein.

Figure 2:
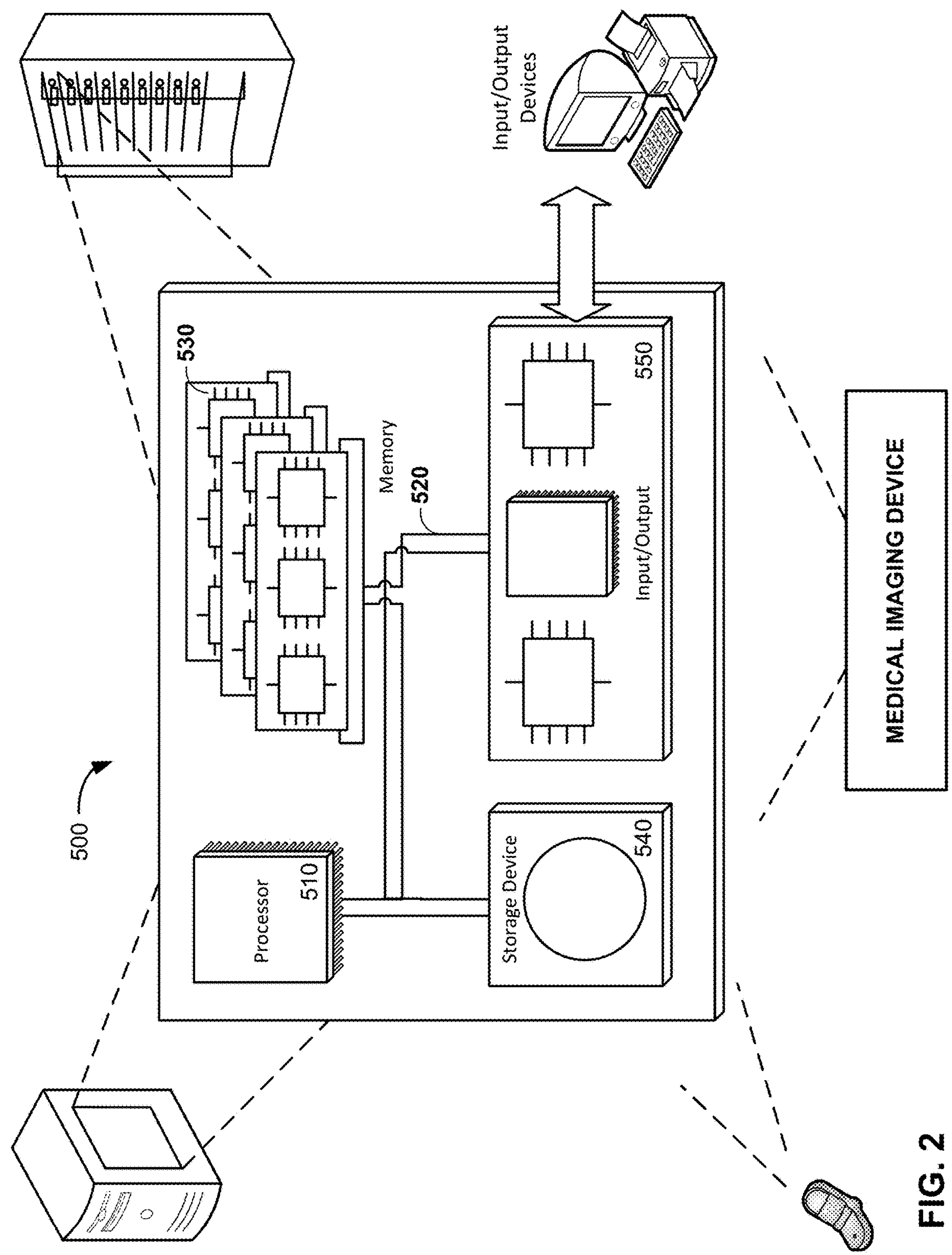
FIG. 2 is a block diagram illustrating an example of various devices that may be configured to implement one or more techniques of the present disclosure.

FIG. 2 is a block diagram illustrating a detailed example of various devices that may be configured to implement one or more techniques of the present disclosure. That is, device 500 of FIG. 2 provides an example implementation for the medical imaging analysis system 10 of FIG. 1. In some examples, device 500 represents medical imaging analysis system 10 implemented as a computing device or computing system, such as a cloud-based computing platform. Device 500 may be a medical imaging device, such as a magnetic resonance imaging (MRI) system, a mobile device (e.g., a tablet, a personal digital assistant, or other mobile device), a workstation, a computing center, a cluster of servers, or other examples of a computing environment, centrally located or distributed, that is capable of executing the techniques described herein. Any or all of the devices may, for example, implement portions of the techniques described herein for generating and outputting predicted prostate cancer visualizations for display.

In the example of FIG. 2, computer-implemented device 500 includes a processor 510 that is operable to execute program instructions or software, causing the computer to perform various methods or tasks, such as performing the techniques for generating and/or using multiparametric models for prostate cancer prediction as described herein. For example, processor 510 provides a computing platform for executing the algorithms of image interpretation module 12, visualization generation module 14 and model generation module of FIG. 1.

In this example, processor 510 is coupled via bus 520 to a memory 530, which is used to store information such as program instructions and/or other data while the computer is in operation. A storage device 540, such as a hard disk drive, nonvolatile memory, or other non-transient storage device stores information such as program instructions, data files of the multidimensional data and the reduced data set, and other information. The computer also includes various input-output elements 550, including parallel or serial ports, USB, Firewire or IEEE 1394, Ethernet, and other such ports to connect the computer to external devices such a printer, video camera, display device, medical imaging device, surveillance equipment or the like. Other input-output elements include wireless communication interfaces such as Bluetooth, Wi-Fi, and cellular data networks.

The computer itself may be a traditional personal computer, a rack-mount or business computer or server, or any other type of computerized system. The computer, in a further example, may include fewer than all elements listed above, such as a thin client or mobile device having only some of the shown elements. In another example, the computer is distributed among multiple computer systems, such as a distributed server that has many computers working together to provide various functions.

In one or more examples, the functions described may be implemented in hardware, software, firmware, or any combination thereof If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media, which includes any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable storage medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

In general, this disclosure describes automatic image registration algorithms that perform three-dimensional (3D), affine, and/or intensity-based co-registration of magnetic resonance imaging (MRI) data, such as multiparametric MRI (mpMRI) data, using mutual information (MI) as a similarity metric. MRI data from multiple imaging series co-registered according to the techniques described herein can be used for development and prospective application of models for computer-aided diagnosis (CAD) systems that perform automated or semi-automated analysis of MRI data.

As one example, multiparametric magnetic resonance imaging (mpMRI), a combination of anatomic and functional MRI techniques, is a useful clinical tool in the detection and diagnosis of prostate cancer. However, interpretation of mpMRI data is difficult and time-consuming, and highly-dependent on observer experience. Computer-aided diagnosis (CAD) systems for prostate cancer are described that are beneficial for accurate and quick diagnosis. However, due to patient motion during the course of a study, as well as distortions inherent to imaging methods, the mpMRI data may be misaligned, which may result in limited accuracy in the systems ability to accurately predict prostate cancer. Systems are described herein that provide technical solutions to the technical problem of potentially misaligned MRI data (e.g., mpMRI data). For example, the systems described herein can improve accurate analysis of mpMRI data through the spatial co-localization of the prostate anatomy in all of the acquired image series.

In some examples, the techniques implemented by the systems of this disclosure may include three parts. A first part of the algorithms may include the definition of a volume of interest (VOI) on which registration parameters may be optimized. The VOI may be obtained automatically, or from radiologists' annotation of a prostate capsule. A second part of the algorithms may include corrections for the presence of an endorectal coil. An endorectal coil is a hardware element used for signal reception in a prostate MRI that also introduces distortions that may confound registration. A third part of the algorithms may include optimization, i.e., finding the best registration parameters via maximization of MI between imaging series. In one example, optimization is primarily carried out using a genetic algorithm.

The techniques of this disclosure may be performed through the execution of software code of an algorithm that performs image registration for prostate mpMRI data sets. The algorithm incorporates methods that improve registration accuracy and robustness.

Although some work has been done on CAD systems for prostate cancer, the registration of mpMRT data is not well-defined. In some examples, registration is often performed manually, or the algorithm is not described in sufficient detail to be reproducible.

This disclosure, proposes techniques for performing 3D, intensity-based registration using an affine transformation model, with MI as the similarity metric. Various example techniques of this disclosure include one or more of the following aspects:

1) Automated or manual segmentation of the prostate capsule to determine the registration volume. Manual segmentation would rely on the use of radiologist's annotation of the prostate capsule. While the process is not automatic, these annotations are already part of the standard clinical workflow for reading prostate MRIs and thus do not require any more work. As image segmentation of medical images is known to be a difficult problem, the registration volume determined using this method is also likely to be no less accurate than that found by any automated method.
2) Compensation for the presence of the endorectal coil (ERC). An ERC is a hardware element that is commonly used in prostate MRI for improved signal reception, but it causes artifacts and distortions on some imaging sequences that can significantly confound registration.
3) Use of a genetic algorithm (GA) to perform the optimization. Compared with gradient descent or quasi-Newton methods, a GA may be more likely to find the global optimum (i.e., the "best" solution in terms of maximization of MI), which translates to better registration results on average.

This disclosure describes an image registration framework that performs 3D, affine, intensity-based co-registration of multiparametric MRI series using mutual information as the similarity metric. The techniques compensate for the effects of an endorectal coil, which is commonly used in prostate MRI. Experiment results to characterize the registration method demonstrated that it is theoretically accurate to within 1.0 mm (when estimating the translation component). Qualitatively, significant improvements are seen in the co-localization of parametric maps with the anatomic images. The framework may, in some example implementations, be integrated into a CAD system for prostate cancer detection.

The performance of computational models for detection of prostate cancer (PCa) using multiparametric MRI (mpMRI) is improved herein by co-registration of imaging series so that parametric maps can be accurately calculated and co-localized. The registration problem is a challenging one. The absence of rigid well-defined structures in the prostate, differences in contrast between imaging series, and potential RF coil dependencies all present technical difficulties. Herein, a semi-automatic framework for 3D affine, intensity-based registration of mpMRI data that provides technical solutions to these challenges is described.

Multiparametric MRI data is used as training data for automated generation of multiparametric cancer model 16.

For examples, a set of patients with known PCa can be captured via mpMRI scans. A combination of a surface array coil and an endorectal coil (ERC) can be used for signal reception.

When generating a multiparametric cancer model 16, model generation module 22 is configured to independently register to the anatomic T2-weighted (T2w) images (target volumes) each of the other imaging series (source volumes). In some implementations, the algorithms applied by multiparametric cancer model 16 involves three major steps.

Step 1: A rectangular volume of interest (VOI) is determined for each patient of the training data, where the specified the subvolume on which registration parameters will be optimized. VOI dimensions were chosen to match the prostate extent, which can be determined via annotation of the prostate capsule by an experienced radiologist. The VOI is defined on target volumes, then propagated to source volumes.

Step 2: The signal intensity inhomogeneity caused by the ERC sensitivity profile is corrected for. This step is advantageous because intensity-based registration may otherwise be biased toward matching coil sensitivity profiles. To perform the correction, the ERC may be modeled as two wires, and the Biot-Savart law was used to calculate the differential contribution of a wire segment to the magnetic field in the xy-plane:

$$d\vec{B} = \frac{I\,\vec{dl} \times \vec{R}}{4\pi|\vec{R}|^3}$$

where $I\vec{dl}$ is the differential element and $\vec{R}$ is the vector pointing from the element to the voxel of interest. All contributions can be summed to obtain the estimated sensitivity profile. After normalization, the sensitivity profile is registered to each of the imaging series using minimum variation as the similarity metric. Maximizing minimum variation may decrease the dispersion of $\log(I_{c,i}/I_{s,i})$ over the defined VOI, where $I_{c,i}$ and $I_{s,i}$ are intensity values of the sensitivity profile and the imaging series, respectively, at voxel i. Lastly, the imaging data can be divided by the aligned sensitivity profile (FIG. 3A-3D). In particular, FIG. 3A-3D are images illustrating intensity correction for the ERC sensitivity profile. FIG. 3A is an axial view of the normalized coil sensitivity profile halfway along the length of the ERC, as estimated from the Biot-Savart law. FIG. 3B is a center axial slice of a T2w anatomic series (intensity uncorrected). FIG. 3C is a coil sensitivity profile from FIG. 3A registered to FIG. 3B, using minimum variation as the similarity metric. FIG. 3D is an intensity-corrected version of FIG. 3B, obtained by dividing FIG. 3C into FIG. 3B on a voxel-wise basis. Images in FIG. 3B and FIG. 3D have the same windowing and level.

Step 3: After intensity correction, data registration module 27 registers each of the source volumes to the target using mutual information as the similarity metric. Multiple echo time turbo-spin echo (TSE) series can be registered directly. For diffusion-weighted imaging (DWI) data, registration may, in some implementations, only performed for the b0 image; the resulting transformation is applied to diffusion-weighted images of different b-values as well as the calculated ADC map. Additionally, due to a chemical shift artifact at the prostate-ERC boundary in the dynamic-contrast enhanced (DCE) data that would otherwise confound intensity-based registration, data registration module 27 may calculate the translation component along the AP axis by calculating the difference between the AP positions of the ERC in the center slice of target and source volumes, which in turn was determined using locally-adaptive thresholding (FIGS. 4A-4D). In particular, FIGS. 4A-4D are images demonstrating the AP translation component for registration of DCE data. FIGS. 4A and 4B are prostate-ERC interface on the center axial slice of the T2w anatomic series and $2^{nd}$ time point of the DCE data, respectively. Arrows 32 indicate features of the ERC that will automatically be co-localized, while the 33 arrow in FIG. 4A indicates the artifact that would otherwise be incorrectly co-localized. FIGS. 4C and 4D are adaptively thresholded versions of FIGS. 4A and 4B, respectively, allowing for the automatic identification of the matching ERC features.

To find the optimal affine transformation in the described registration tasks, data registration module 27 may apply a two-step algorithm to address the non-convexity of the optimization problem. First, data registration module 27 may apply a genetic algorithm, using fitness-proportionate selection with a small mutation operator, to find candidates for the best mapping. Data registration module 27 then applies an iterative grid search used to sweep for potential local maxima near each candidate.

As such, as described herein, technical solutions are described for automatically generating spatially co-registered data from a collection of different kinds of medical imaging scans of patient tissue that utilized, for example, different contrasts during the imaging process. The techniques presented herein select one of the scans as a "target" scan (series) and, independently for each of the other "source" scans (series), generate a 3D mapping function which relates any point in a subregion of interest in the target scan to a point in the source scans which corresponds to the same material point in the body of the patient. Such a map for each of the source fields can then be used to obtain co-registered values of all fields on the mesh of the target field.

While the finite resolution, limited signal to noise ratio, and the infinite dimensional space of all possible 3D mappings make perfect target to source maps impossible, good approximations can be obtained in a finite dimensional subspace of maps. A map in this subspace is expressed in terms of parameters, with one parameter per each dimension of the subspace. Many parameter spaces of mappings are possible, and different ones may be better suited for registering different pairs of scans. Several parameterizations of a linear 3×3 transformation plus shift are discussed in further detail below as examples. However, the method for finding the best map is designed to take any user defined parameter space of mappings. The mapping routine takes the parameters of a given map, along with a set of points in the target space and produces values from the source field at the mapped points. The mapped points will not generally be exactly at voxel centers in the source scan, and interpolation can be applied. The kind of interpolation used is considered a part of map implementation. Here, both nearest neighbor and trilinear interpolation are used, as examples.

An optimal set of parameters is defined herein in terms of a metric function that measures goodness of fit. Many metric functions are possible, and different metric functions may be best suited for different pairs of scans. Also, goodness of fit may be based on the original scan fields, or derived fields which emphasize different structural characteristics in the scans. The method discussed here can take any user defined metric function on raw or derived fields. The only restriction is that the metric returns a scalar value that increases with goodness of fit for the two input fields provided as values on the same mesh. Examples of metric functions implemented and tested so far are based on chi-squared, mutual information, and minimum variation.

For a given pair of source and target fields, region of interest in the target space, parameter space of maps, and metric function, best fit parameters may be found. A list of points and corresponding values in the region of interest in the target scan are collected. Next, a genetic algorithm is used to find parameters that maximize the metric function between the target values in this list and values of the corresponding mapped points in the source field. The genetic algorithm works by iterating on a population of parameters. The initial population of parameters is a random sampling in the parameter space, within user specified bounds on each parameter. A metric value is generated for each parameter set (i.e., n-tuple of parameters which specify a unique map). The next generation is comprised of "children" of the parameter sets with the highest scores. For each parameter set, the number of children increases, and the spread of parameter values of those children decreases, with metric score. Populations are iterated in this way till the distribution of population scores stops improving, or a maximum number of iterations is reached. With the right set of parameters controlling the number of children and closeness of characteristics based on scores, usually only a few dozen iterations are needed to find a fairly good fit that is close enough to optimal to be in the globally best region of parameter space. Then a grid search is used to find the best fit parameter set.

This best fit parameter set, along with the definition of the map in terms of these parameters, can be used in external applications to co-register the fields in any of a variety of ways. For convenience, an example registration application is provided, which produces source values at each mesh location of the target. It uses the same mapping routines that were used to generate the optimal set of parameters, which guarantees consistency. It supports both nearest neighbor and trilinear interpolation for the mapping.

Scans are often strongly influenced by a coil used to improve the local signal. The effect of the coil is to amplify the value of the scan by a coil function, which becomes a very large factor and varies rapidly near the coil. Since the location of the coil relative to the structures of interest varies from scan to scan, attempts to register two scans can be skewed, or even dominated, by the strong variations imposed by the coil. Registrations can be greatly improved by dividing each scan by an effective coil gain function. A template coil gain function is provided on a finely sampled raster of points. This raster can be co-registered to a particular scan by using the techniques described above. Here, the raster of template coil gain values is treated as the source field, and the scan data to be normalized is treated as the target field. The region of interest in the scan field is selected to include the locations of largest variation, where the coil effect is the strongest. The least variation metric function is used for goodness of fit. This function increases inversely with the dynamic range of the ratio of target to source fields, so that the best fit location of the coil corresponds to the resulting "normalized" scan field having the least variation. Optimal parameters are found using the same search method as described above, and then used to generate a co-registered coil gain function. This is then divided into the scan field, point by point, to produce a normalized gain field.

Details of the available mapping parameter spaces, metric functions, region of interest, and phases of the search algorithm (genetic and grid), along with input specifications for each, are described below. Example file formats, conversion routines, coordinate systems used, and examples of the entire registration process are also given in what follows.

Coordinates, Regions, and Mappings

As one example, a DCM file is an image file saved in the Digital Imaging and Communications in Medicine (DICOM) image format. It stores a medical image, such as a MRI data, CT scan data or ultrasound data.

The coordinates used to specify a point in each scan match as closely as possible those given in the corresponding scan files. Here we use (X,Y,Z) for the coordinates of a point. DCM files include dx and dy pixel spacing, (Nx, Ny) for the number of pixels in each direction, and a third coordinate, $Z_k$ where k=1, 2, . . . , Nz, for the displacement of the plane of the scan. Since offsets in x and y are not specified, and scans are usually closely centered on structures of interest, the range of X and Y coordinates are centered on the scan. Scan values are given on a mesh, which reflect an integral of some point spread function around the point. Hence, the ($X_i$, $Y_j$, $Z_k$) coordinates of the (i,j,k) voxel in stack of DCM files are $$(X_i,Y_j,Z_k)=(dx*(i-1)-L_x/2,dy*(j-1)-L_y/2,Z_k)$$

Here, $L_x$=dx*Nx, $L_y$=dy*Ny. In general, $Z_k$ is the coordinate read from the DCM file. However, so far the Z coordinates increase uniformly in the stack of DCM file, so it is assumed that we can write $$Z_k=Z_1+dz*(k-1)$$

and for the the array of values in each scan are assumed to be associated with a regular 3D array of points.

A region of interest is used to specify a subvolume of the target scan to be used in finding the best fit map. Only target mesh points in this subvolume are used for the fit. Currently, only rectangular subvolumes, aligned with the XYZ mesh, are supported. This 3D block is specified by its' center and size in the input file with lines like

| | | | |
|---|---|---|---|
| blkcntr | 0.0 | 0.0 | 0.0 |
| blksize | 80.0 | 60.0 | 27.0 |

Here, the line starting with blkcntr has the XYZ coordinates of the center of the block, and the line starting with blksize has the XYZ length, width and height of the block. Both are in the coordinates of the target scan, as described above. By using the same region of interest in the target scan to find maps for each of the source scans, all of the maps are optimized for generating source values on the same set of points on the target mesh.

Since the techniques produce estimates of values of all scans on the same "target" mesh, the convention used here is to specify maps of points in the target volume to points in the source volume. Then the desired source values can be evaluated from the mapped points via whatever kind of interpolation is appropriate. Currently, maps consisting of a linear transformation plus a 3D shift are supported. To improved convergence of iteratively find the best fit, it is useful to maximize the independence of the shift and the 3D transform. This is done by centering the 3D transform at the center of the region of interest: so that a 0 vector shift leads to the region of interest being rotated and expanded about its' center. Such a map can be written as $$\vec{S}=\vec{\vec{A}}\cdot(\vec{T}-\vec{C})+\vec{C}+\vec{\delta S}$$

Here, $\vec{S}$ is the 3D point in coordinates of the source scan, $\vec{A}$ is a 3×3 transformation matrix, $\vec{T}$ is the 3D point in coordinates of the target scan, $\vec{C}$ is the center of the block specified by blkcntr (see above), and $\overrightarrow{\delta S}$ is the vector shift.

Two parametrizations of the linear transform plus shift map are currently available. Both support all twelve degrees of freedom. In the default parameterization (referred to as A33 and used if no other is specified) the first nine parameters are just the components of the 3×3 matrix (in row then column order), and the last three are the XYZ components of the shift. For any given map, these twelve parameters are internally passed in a 1D array $$[A_{11},A_{21},A_{31},A_{12},A_{22},A_{32},A_{13},A_{23},A_{33},\delta S_1,\delta S_2,\delta S_3]$$

If this A33 parameterization is used, ranges for each of the twelve parameters to be used in the search for best fit can be specified as follows:

| | | | |
|---|---|---|---|
| maxdefor | <ΔA> | | |
| maxshift | <ΔS1> | <ΔS2> | <ΔS3> |

The first line imposes ranges for each of the components of the 3×3 transform matrix to be $$A_{ij}\in[\delta_{ij}-\Delta A,\delta_{ij}+\Delta A]$$

where Kronecker delta, $\delta_{ij}$, is 1 if i=j and 0 otherwise. The second line imposes ranges for the XYZ components of shift to be $\delta S_i\in[-\Delta S_i, \Delta S_i]$.

For any given parametrization, the search for best fit is free to try any map which has each parameter within its' own range—independent of any of the other parameters. This independence of parameters not only leads to simplicity and better performance (per map tried) of the search algorithm, but also allows the user to specify how to restrict the search for maps by choosing which parametrization. For example, the A33 parametrization might be optimal if shear, twist, anisotropic expansion or compression, and rotation were expected to all have comparable effects on the map. However, aside from the 3D shift, rotations dominate the map, followed by some expansion factor (either isotropic or in one direction because of a peculiar scaling of the scan), and effects of twist and shear are negligible. For these considerations, a second parameterization, which explicitly constrains rotations and expansions, is available and described below.

The RPY parametrization expresses the 3D transform matrix in terms of a rotation and independent expansion and compressions in three orthogonal directions. Rotation is parameterized in terms of three Euler angles: roll (ϕ around the X-axis), pitch (θ around the Y-axis), and yaw (Ψ around the Z-axis). The rotation matrix $\overset{=}{R}(\phi, \theta, \Psi)$ performs these three extrinsic axis rotations in the order of roll, then pitch, then yaw. The three orthogonal directions for expansion or compression are specified in terms of similar Euler angles ($\phi_s$, $\theta_s$, $\Psi_s$). The expansion and compression factors are expressed in terms of an isotropic factor $\alpha_0$, with independent multiplicative factors along the 1st and 2nd directions ($\alpha_1$ and $\alpha_2$). The full set of RPY parameters, including the final vector shift, are $$[\phi,\theta,\Psi,\alpha_0,\alpha_1,\alpha_2,\phi_S,\theta_S,\Psi_S,\delta S_1,\delta S_2,\delta S_3]$$

Deformations along the three chosen directions are applied first, and then the rotation is applied, so the corresponding 3×3 transformation matrix is $$\overset{=}{A}_{RPY}=\overset{=}{R}(\phi,\theta,\Psi)\cdot\overset{=}{R}(\phi_S,\theta_S,\Psi_S)\cdot(\alpha_0\alpha_1\hat{x}\hat{x}+\alpha_0\alpha_2\hat{y}\hat{y}+\alpha_0\hat{z}\hat{z})\cdot\overset{=}{R}^{-1}(\phi_S,\theta_S,\Psi_S)$$

and the full map from a point $\vec{T}$ in target space to the point $\vec{S}$ in source space, with block center $\vec{C}$ as before, is $$\vec{S}=\overset{=}{A}_{RPY}\cdot(\vec{S}-\vec{C})+\vec{C}+\overrightarrow{\delta S}$$

The RPY parameter space is selected with the keyword RPY_map, which, like other keywords, can appear on any line in the input file, but the line must start with the keyword. These keywords, along with their inputs for setting the ranges for all the RPY parameters are

| | | | |
|---|---|---|---|
| RPY_map | | | |
| RPY_min | <$\Phi_{min}$> | <$\theta_{min}$> | <$\Psi_{min}$> |
| S12_min | <$a_{0\ min}$> | <$a_{1\ min}$> | <$a_{2\ min}$> |
| SRPY_min | <$\Phi_{s\ min}$> | <$\theta_{s\ min}$> | <$\Psi_{s\ min}$> |
| shift_min | <$S_{1\ min}$> | <$S_{2\ min}$> | <$S_{3\ min}$> |
| RPY_max | <$\Phi_{max}$> | <$\theta_{max}$> | <$\Psi_{max}$> |
| S12_max | <$a_{0\ max}$> | <$a_{1\ max}$> | <$a_{2\ max}$> |
| SRPY_max | <$\Phi_{s\ max}$> | <$\theta_{s\ max}$> | <$\Psi_{s\ max}$> |
| shift_max | <$S_{1\ max}$> | <$S_{2\ max}$> | <$S_{3\ max}$> |

For each of the 12 RPY parameters, Q, the range is set to $[Q_{min}, Q_{max}]$. If $Q_{mon}$ is not specified in the input file, then the default is a symmetric range around 0: $Q_{min}=-Q_{max}$, except for the three expansion factors, where the default is a symmetric factor around unity: $\alpha_{i\ min}=1/\alpha_{i\ max}$, for i=1, 2, 3.

Metric scores for goodness of fit Given a (target, source) pair of scans, with their respective coordinate systems from their DCM files, a region of interest in target coordinates, and a specific map $\vec{S}=\vec{M}(\vec{T})$ from target coordinates to source coordinates, a metric (or score) function is used to evaluate how well the map registers the source data to the target mesh. Source and target 3D fields need not be simply or linearly related to scans. All that is needed is that values of each of these fields are given on a 3D regular mesh of points that are registered to XYZ coordinates.

As examples, chi-squared, mutual information, and minimum variation metrics are described in details as examples for use by the algorithms described herein. All three work on the same data structure and produce values which increase with goodness of fit. The data they use are N pairs of values $$\{(V_T(\vec{T}_i),V_S(\vec{S}_i)):i=1,\ldots,N\}$$

where $\vec{T}_i$ for i=1, . . . , N, are the N mesh points in the region of interest in target space, $\vec{S}_i\equiv\vec{M}(\vec{T}_i)$ are the corresponding points in source space according to the ame M, and target and source scan values at points in their respective spaces are given by the functions $V_T$ and $V_S$ respectively. Since the points $\vec{T}_i$ correspond to mesh points (or centers of mesh voxels) in the target scan, The values $V_T(\vec{T}_i)$ correspond directly to the scan values. The mapped points $\vec{S}_i$ do not generally match mesh points of the source scan, and some kind of interpolation is needed. Tri-linear interpolation is used for finding optimal maps.

Chi-Squared Metric

Given N pairs of values ($V_{Ti}$, $V_{Si}$), where $V_{Ti}=V_T(\vec{T}_i)$ and $V_{Si}=V_S(\vec{S}_i)$, the chi_squared metric is $$G_{\chi}2 = \frac{\sum_{i=1}^{N}(V_{Ti}-\overline{V}_T)(V_{Si}-\overline{V}_S)}{\sqrt{\sum_{i=1}^{N}(V_{Ti}-\overline{V}_T)^2}\sqrt{\sum_{i=1}^{N}(V_{Si}-\overline{V}_S)^2}}$$

where $\overline{V}_T$ and $\overline{V}_S$ are the averages of the N target and source values used, respectively. Given any variation in both source and target values, this metric produces values in the range $G_{\chi}2\in[-1, 1]$. The Chi-squared metric is parameter free, and is the default metric which is used if no other metric is specified in the input file.

This metric is effective for finding optimal maps if the source and target values used are expected to be highly correlated at the same material points. Raw scan values may increase, decrease or be fairly constant over a given set of material locations, depending on the contrast of the scan. Hence, the chi-squared metric may only be effective on derived fields, such as those designed to detect edges of structures or other geometrical features.

Mutual Information Metric

Another metric is based on the mutual information in the pairs of target and source values. The metric score is normalized by the entropy of the target data. Evaluation of both mutual information and entropy require binning both source and target data. Given bin size $\delta V_T$, bin offset $V_{0T}$, and number of bins $N_T$, the set of target values on the 3D mesh in the region of interest $\{V_{Ti}: i=1, \ldots, N\}$, are binned into an array $P_T(j)$ according to $$P_T(j) = \frac{1}{N}\sum_{i=1}^{N}\delta_{j,1+int((V_{Ti}-V_{0T})/\delta V_T))}$$

where int(x) is the integer part of x. Similarly, with independent bin size, offset, and number, $\delta V_S$, $V_{0s}$, $N_S$, source values are binned into $$P_S(j) = \frac{1}{N}\sum_{i=1}^{N}\delta_{j,1+int((V_{Si}-V_{0S})/\delta V_S))}$$

and pairs of values ($V_{Tt}$, $V_{St}$) are binned into the 2D array $$P_{TS}(j,k) = \frac{1}{N}\sum_{i=1}^{N}\delta_{j,1+int((V_{Ti}-V_{0T})/\delta V_T))}\delta_{j,1+int((V_{Si}-V_{0S})/\delta V_S))}$$

With the right bin sizes and offsets, ranges of bin indexes with be in [1, $N_T$] for target, and in [1, $N_S$] for source data. Given this binned data, the entropy for the target data is $$E_T = -\sum_{i:\,P_T(i)\neq 0} P_T(i)\log_2(P_T(i))$$

and the mutual information between target and source is $$I_{TS} = \sum_{(i,j):\,P_{ts}(i,j)\neq 0} P_{TS}(i,j)\log_2\left(\frac{P_{TS}(i,j)}{P_T(i)P_S(j)}\right)$$

The score returned by this mutual information metric is the mutual information between target and scan data, in the region of interest, normalized by the entropy of the target data in the same region of interest:

$$G_{MI}=I_{TS}/E_T$$

With this normalization, the mutual information score is in [0, 1]. Also, the normalization factor is independent of the map, so that for a given target scan and region of interest, the best score corresponds to the best mutual information: normalizing by the entropy is only a convenience in that it ensures scores are in an expected range.

Minimum Variation Metric

The minimum variation metric is a measure of how well source data can be used to reduce the variation in target data with a given mapping. This score is primarily used to find the registration of a model coil gain function to any given scan data in order to remove large variations in scan data due to proximity to the coil. The usual set of value pairs $\{V_{Ti}, V_{Si}), i=1, \ldots, N\}$ generated for a given target to source map are used, and optimal map minimizes the range of variation of $V_{Ti}/V_{Si}$ at locations where the target values are non-negligible. A threshold, $V_{min}$, for negligible values is used: only target locations in the region of interest where $V_{Ti}>V_{min}$ are used in evaluating the metric. The minimum variation score is based on the dispersion of $\log(V_{Ti}/V_{Si})$ around its average. With the normalized weight $$w_i = \frac{1}{w_{total}}\max(0, V_{ti}-V_{min}),$$

where $$w_{total} = \sum_{i=1}^{N}\max(0, V_{Ti}-V_{min}),$$

the weighted averages $$\overline{V_T^k} = \sum_{i=1}^{N} w_i \log(V_{Ti}^k), \text{ and } \overline{R^k} = \sum_{i=1}^{N} w_i \log\left[\left(\frac{V_{Ti}}{V_{Si}}\right)^k\right]$$

for k=1 and 2 are used to evaluate the minimum variation score $$G_\sigma = 1 - \frac{\overline{R^2} - \overline{R^1}^2}{\overline{V_T^2} - \overline{V_T^1}^2}$$

This metric increases with decreasing variation of $V_{Ti}/V_{Si}$, is always ≤1,and is usually in the range [0,1]. This metric is selected, and the threshold parameter $V_{min}$ is set with the keyword/value line

| | |
|---|---|
| min_var | <$V_{min}$> |

in the input file.

Search for Best Fit Mapping

Given source and target data with their respective coordinate systems, a region of interest in target space, a parametrization of maps from target to source space, and a choice of metric score for evaluating the goodness of fit for any given map, an optimal map is found via a genetic algorithm followed by a grid search. Both searches simply optimize the metric score G as a function of the n-tuple of mapping parameters $(p_1, \ldots, p_n)$. This metric score can be written as $$G(p_1, \ldots, p_n)=G_?[\{V_{Ti}, V_S(\dot{M}(\dot{T}_i, p_1 \ldots, p_n)):i=1,N\}]$$

where $G_?$ is one of the metrics described above. With source and target data, region of interest, and the parametrized family of maps $\vec{M}(\ldots)$ all held fixed, G is seen to be only a function of the parameters $p_k$. In this way, the search algorithms only work with values retuned by the score function G as they search through the the space of n-tuples in their respective ranges: $p_{range}=\{(p_1, \ldots, p_n): p_k \in [p_{k,min}, p_{k,max}], k=1, \ldots, n\}$ as specified in the input file by {maxdefor, and maxshift} for the A33 family of maps, or by {RPY_max, S12_max, SRPY_max, and shift_max} for the RPY family of maps, as described above.

Genetic Algorithm

Example implementations of the genetic algorithm are described below.

The genetic algorithm (GA) iterates a population of $N_p$ n-tuples of parameters. The initial population is a random sampling in $p_{range}$. A pseudo random number generator is used for this and subsequent random distributions, The random number sequence is initialized with an integer seed $I_{seed}$. Population size and random number seed are set in the input file with the keyword-value lines|

| | |
|---|---|
| npop | <$N_p$> |
| seed | <$I_{seed}$> |

The iterative step takes each "generation" (i.e., the population at a given iterative step) to the next generation by replicating (with "small" random variations) parameter n-tuples with the highest metric scores, while keeping the population size $N_p$ fixed. The number of "children", $N_{Ci}$, that the i-th n-tuple of parameters $\vec{p}_i$, contributes to the next generation increases with its metric score, $s_i=G(\vec{p}_i)$, according to $$N_{Ci} = \text{int}\left[\frac{1}{2} + \frac{N_p}{f_{total}}(r_\varepsilon + r_i)^{\gamma_s}\right]$$

$$\text{where } r_i = \max\left(0, \frac{s_i - s_{min}}{s_{max} - s_{min}}\right) \text{ and } f_{total} = \sum_{i=1}^{N_p}(r_\varepsilon + r_i)^{\gamma_s}$$

As written, $$\sum_{i=1}^{N_p} N_{ct}$$

will be close to $N_p$. To ensure that the population does not change in size, the number of children is increased or decreased by 1 as needed for a few "parents" who had one or more children. in these formula $r_e$, $S_\gamma$, $S_{min}$, and $S_{max}$ are ail constant parameters specified in the input file with the keyword-value lines.

| | |
|---|---|
| score_eps | <$\gamma_\varepsilon$> |
| score_pow | <$\gamma_s$> |
| score_min | <$S_{min}$> |
| score_max | <$S_{max}$> |

Parameters $p_{cj} \in [p_{j,min}, p_{jmax}]$ for j=1, . . . , n of each child are correlated with their parent's parameters $p_{Pj}$ according to the probability distribution $$p_{Cj} = \frac{1}{f_{\delta f}}\exp(-|p_{Cj} - p_{Pj}|/\delta_P) \text{ where } f_{\delta j} = \int_{p_{j,min}}^{p_{j,max}} \exp(-|p - p_{Pj}|/\delta_P)\,dp$$

The spread of this probability distribution, $\delta_p$, decreases with increasing parent metric score, s, according to $$\delta_P = \delta_{max}\left(f_\varepsilon + \frac{s_{max} - s}{s_{max} - s_{min}}\right)^{\gamma\delta}$$

The constants, $\delta_{max}$, $f_\varepsilon$, and $\gamma_\delta$ are set in the input file keyword-value lines

| | |
|---|---|
| dpf_eps | <$f_\varepsilon$> |
| dpf_pow | <$\gamma_\delta$> |
| dpf_max | <$\delta_{max}$> |
| init_dp_fac | <$\delta_{P,\ init}$> |

Note that $s_{min}$ and $s_{max}$ used here are the same input constants discussed above. Minimum and maximum number of iterations of this GA are specified with the input lines

| | |
|---|---|
| miniter | <$N_{iter,\ min}$> |
| maxiter | <$N_{iter,\ max}$> |

After $N_{iter,min}$ iterations, the GA will stop if the distribution of scores stops changes significantly, or after a total of $N_{iter,max}$ iterations whichever comes first.

Grid Search

The genetic algorithm (GA) search described here efficiently finds the region of parameter space with the global minimum. For the final best fit, a simple grid search can be used to increase speed. This search starts with the set of parameters with the highest score in the last generation from the GA search.

Then for each of the parameter components, $p_k$, with a non-vanishing range (i.e., $p_{k,min}<p_{k,max}$) the parameter component is incremented by a small fraction of the range for that component $\delta p_k=f_{grid}(p_{k,max}-p_{k,min})$ holding all the other parameter components fixed until a maximum score is found in this sweep direction. Unless otherwise specified, parameter ranges used in the GA search are imposed during the grid search, which can lead to the grid search finding a fit outside the range of parameters. Either way, if a bound is reached, then the method reports this to warn the user that a larger range for this parameter component may be needed. Each of the parameter components are individually tuned in this way. If any of the parameters change, then the process is repeated: each of the parameter components are individually tuned on the same grid, starting from the components from last set of tunings. This is iterated till none of the components change.

Upon completion, grid search then stops and the tuned components from the final pass is returned as the best fit found. Currently, $f_{grid}=0.01$, which could easily be adjusted or made into a input parameter. Further, the techniques could be used in a hierarchical grid search, where the grid search is repeated with $f_{grid}$ decreasing by a factor of 10, for example, each time.

Experimental Results

Thirty-four patients with known PCa were given mpMRI scans at 3T. Multiparametric MRI data was acquired using technique described in Metzger et. al, Detection of Prostate Cancer: Quantitative Multiparametric MR Imaging Models Developed using Registered Correlative Histopathaology, Radioology, 2016; 279(3): 805-16.

Imaging sequence parameters used for capturing the multiparametric MRI are shown in Table 1.

TABLE 1

| | T2w anatomic | T2 mapping | DWI | DCE-MRI |
|---|---|---|---|---|
| Sequence | TSE | TSE | Single-shot EPI | GRE |
| Echo time (ms) | 107 | 36, 71, 142 | 88 | 1.44 |
| Nominal voxel size (mm) | 0.61 × 0.55 × 3 | 0.61 × 0.55 × 3 | 1.41 × 1.41 × 3 | 1.35 × 1.45 × 4 |
| Temporal resolution (s) | — | — | — | 6 |
| b values (s/mm$^2$) | — | — | 50, 400, 800 | — |

ADC maps were calculated from the DWI data. DCE-MRI data were acquired over 5 minutes, resulting in 50 dynamic volumes. Pharmacokinetic maps were generated using a modified Toft model.

To validate the described techniques, random affine transformations T were applied to select source volumes that were deemed to be aligned (without registration) with the corresponding target volumes. The transformations $\hat{T}$ that would bring transformed source volumes back into alignment were estimated, and distances between $T^{31\ 1}$ and $\hat{T}$ (ideally 0) were quantified using the Frobenuis norm (Table 2).

TABLE 2

| | Source volume | | |
|---|---|---|---|
| Frobenius norm | TSE (TE = 36) | DWI (b0) | DCE (pre-contrast) |
| Mean | 0.37 (n = 10) | 0.84 (n = 6) | 0.62 (n = 7) |
| Max | 0.47 | 1.01 | 0.93 |

In particular, Table 2 demonstrates the reliability of the proposed registration methods. Random transforms (T) were applied to source series that were already aligned without need of registration. The distance between the estimated ($\hat{T}$) and true ($T^{-1}$) inverse transforms were quantified using $\|\hat{T}-T^{-1}\|_F$, where $\|\cdot\|_F$ denotes the Frobenius norm. The average and maximum distance between $\hat{T}$ and $T^{-1}$ are shown for representative source volumes. Because translation components of the transforms dominate, it may be concluded that the registration method has a maximum error of ±1.0 mm when estimating the translation components.

Figure 5A:
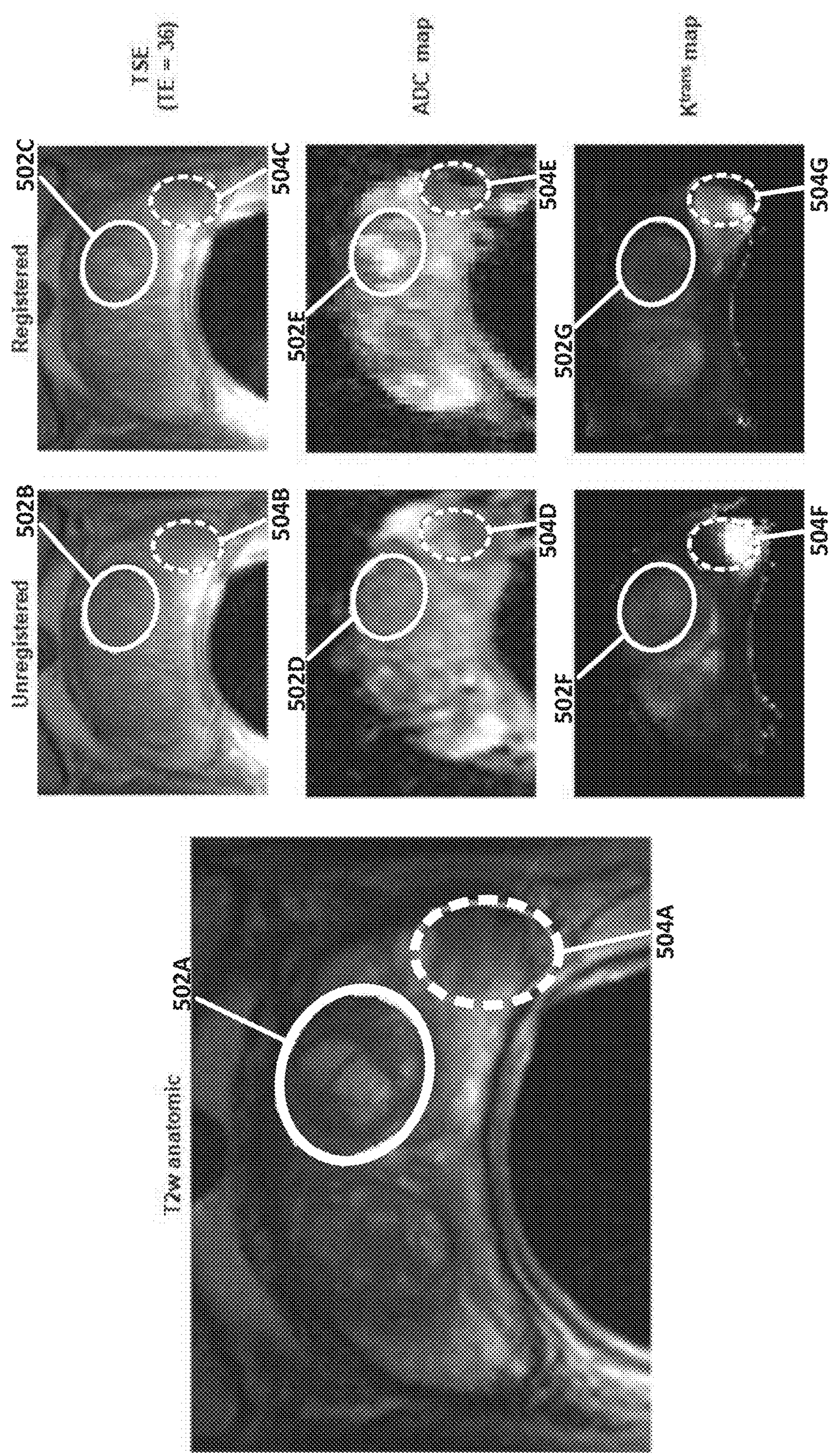
FIG. 5A is a set of images in which regions of interest (ROIs) drawn on an axial slice of the T2w anatomic series and propagated to both unregistered and registered source volumes. In this case, co-localization of both the anatomic landmark (ROIs indicated by solid rings 502A-502G) and the region suspicious for cancer (ROIs indicated by dashed rings 504A-504G) is clearly superior after registration utilizing example techniques described in this disclosure.
Figure 5B:
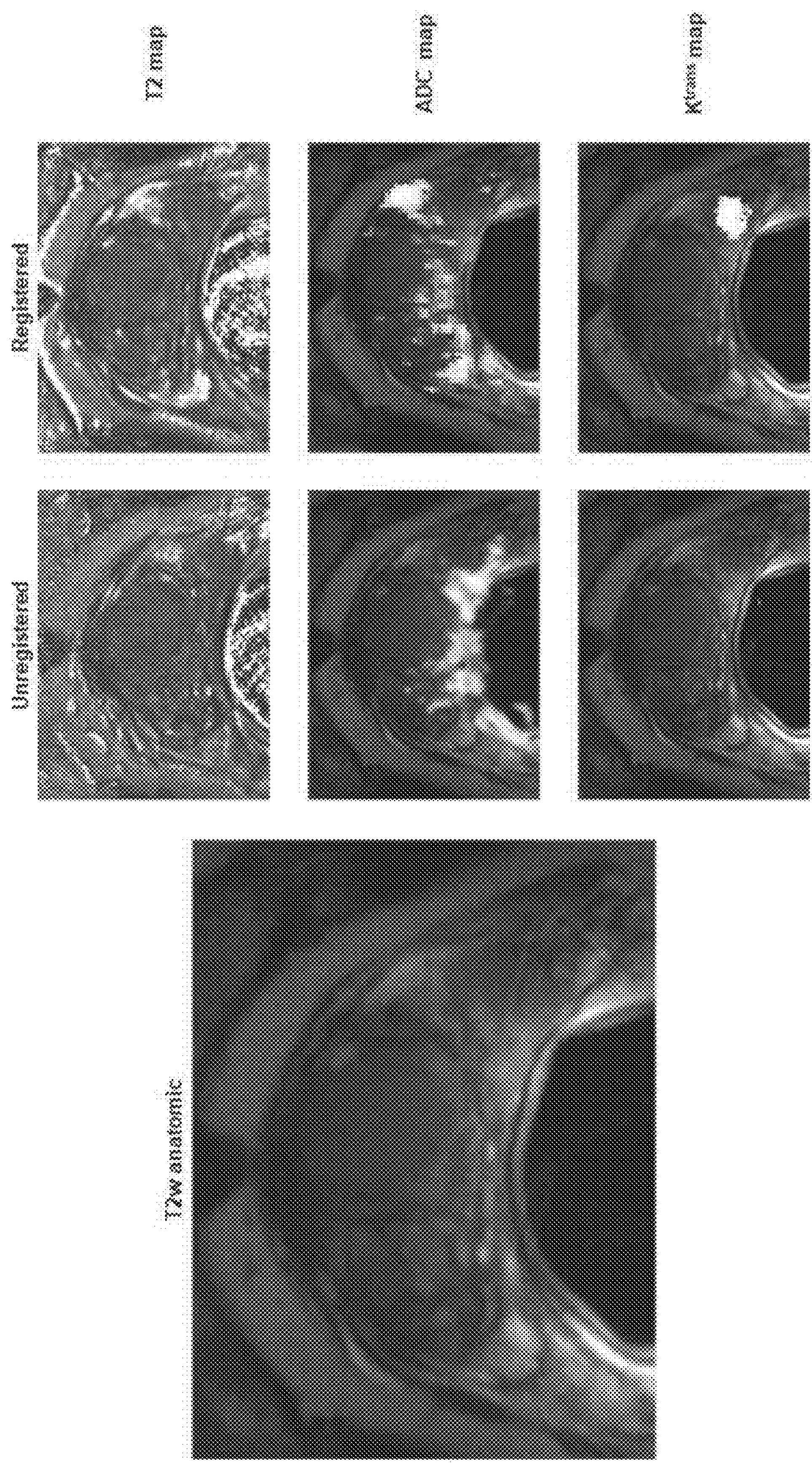
FIG. 5B are images showing unregistered and registered maps, with ADC and $K^{trans}$ maps overlaid on the corresponding axial slice of the T2w anatomic series (different slice than in FIG. 5A).

To visually assess registration quality, cases that had obvious misalignment were identified. For each case, ROIs were identified and manually outlined on the target volume, the propagated to the source volumes before and after registration. FIGS. 5A-5B show the results plus registered parametric maps for a representative case. In particular, FIG. 5A is a set of images in which regions of interest (ROIs) drawn on an axial slice of the T2w anatomic series and propagated to both unregistered and registered source volumes. In this case, co-localization of both the anatomic landmark (ROIs indicated by solid rings 502A-502G) and the region suspicious for cancer (ROIs indicated by solid rings 502A-502G) is clearly superior after registration with the proposed methods. FIG. 5B are images showing unregistered and registered maps, with ADC and $K^{trans}$ maps overlaid on the corresponding axial slice of the T2w anatomic series (different slice than in FIG. 5A).

The experimental results demonstrated that the algorithms can reliably compensate for affine distortions in source volumes, which can help produce higher-quality parametric maps. Although the tests used an ERC, the techniques can be adapted to non-ERC studies as well. Moreover, the techniques can readily be extended to a multi-resolution approach, which may improve the speed and accuracy of the optimization process.

Various examples have been described. These and other examples are within the scope of the following claims.

What is claimed is:

1. A method comprising:

receiving, by a computing device, a plurality of imaging series of magnetic resonance imaging (MM) data for imaged tissue of a patient;

identifying, by the computing device, a volume of interest (VOI) of each image of the imaging series of the MM data;

computing, by the computing device and using a genetic algorithm applied to the VOIs, registration parameters for the VOIs through a maximization of mutual information of the VOI; and registering, by the computing device, the VOIs of the images of the plurality of imaging series using the computed registration parameters.

2. An apparatus comprising:

a non-transitory computer-readable storage medium storing a plurality of imaging series of magnetic resonance imaging (MRI) data for imaged tissue of a patient; and a processor coupled to the computer-readable storage medium;

wherein the processor is configured to receive the imaging series of MRI data;

identify a volume of interest (VOI) of each image of the imaging series of MRI data;

compute, using a genetic algorithm applied to the VOIs, registration parameters for the VOIs of the plurality of imaging series through the maximization of mutual information of the VOIs; and register the VOIs of the plurality of imaging series using the computed registration parameters.

3. A non-transitory computer-readable storage medium storing instructions that, when executed, cause one or more processors to:

receive images comprising magnetic resonance imaging (MRI) data for imaged tissue of a patient;

correct, by the computing device, signal inhomogeneities in one or more volumes of interest (VOI) for the images;

compute, using a genetic algorithm applied to the VOIs, registration parameters for the corrected VOIs through the maximization of mutual information of the corrected VOIs; and register, by the computing device, the VOIs using the computed registration parameters;

apply a multiparametric model to the registered VOIs to generate a Composite Biomarker Score (CBS) map that maps the imaged tissue using a respective CBS value for one or more voxels of the imaged tissue;

determine locations of the CBS map that correspond to CBS values that satisfy a threshold;

generate a visual indication of the determined locations of the CBS map as regions of the imaged tissue predicted to include cancer; and output the visual indication.

4. A method comprising:

receiving, by a computing device, a plurality of imaging series of magnetic resonance imaging (MM) data for imaged tissue of a patient;

identifying, by the computing device, a volume of interest (VOI) of each image of the imaging series of the MM data;

correcting, by the computing device, distortions that affect intensity values in each of the VOIs caused by signal inhomogeneities due to the presence of the endorectal coil (ERC) in each of the VOIs to generate corrected VOIs, wherein correcting the distortions comprises:

modeling the ERC as two parallel wires perpendicular to an axial imaging plane of the imaged tissue;

calculating a differential contribution of each wire segment to a magnetic field in the xy-plane for each of the VOIs;

summing the differential contributions to obtain a coil sensitivity profile for each of the VOIs;

registering the sensitivity profile for each of the VOIs to the respective imaging series using a minimum variation metric as a similarity metric; and dividing the intensity values of the imaging series by the respective registered coil sensitivity profile on a pixel-wise basis;

computing, by the computing device, registration parameters for the corrected VOIs through a maximization of mutual information of the corrected VOIs; and registering, by the computing device, the corrected VOIs of the images of the plurality of imaging series using the computed registration parameters.

5. The method of claim 1, wherein the plurality of imaging series of MRI data is of a prostate.

6. The method of claim 1, further comprising:

capturing the plurality of imaging series of MRI data using a combination of a surface array coil and an endorectal coil (ERC).

7. The method of claim 1, further comprising:

segmenting a prostate capsule on the imaging series.

8. The method of claim 7, wherein identifying, by the computing device, the VOI of each image of the imaging series of the MRI data comprises determining dimensions of the VOI based on the segmented prostate capsule.

9. The method of claim 1, wherein the MRI data comprises multiparametric magnetic resonance imaging (mpMRI) data.

10. The method of claim 1, further comprising:

prior to computing the registration parameters, correcting, by the computing device, distortions that affect the intensity values in each of the VOIs caused by signal inhomogeneities due to the presence of the endorectal coil (ERC) in each of the VOIs.

11. The method of claim 10, wherein correcting, by the computing device, the distortions that affect the intensity values in each of the VOIs comprises:

modeling the ERC as two parallel wires perpendicular to an axial imaging plane of the imaged tissue;

calculating a differential contribution of each wire segment to a magnetic field in the xy- plane for each of the VOIs;

summing the differential contributions to obtain a coil sensitivity profile for each of the VOIs;

registering the sensitivity profile for each of the VOIs to the respective imaging series using a minimum variation metric as a similarity metric; and dividing the intensity values of the imaging series by the respective registered coil sensitivity profile on a pixel-wise basis.

12. The method of claim 1, wherein computing, by the computing device, the registration parameters for the VOIs through the maximization of mutual information of the VOIs comprises:

identifying a target imaging series and a source imaging series from the plurality of series of prostate MRI data; and determining an affine transformation to map points in each VOI in the images of the target imaging series to the source imaging series.

13. The method of claim 12, wherein determining, by the computing device, registration parameters for the affine transformation comprises:

applying the genetic algorithm to the VOIs to find candidates for the registration parameters, the genetic algorithm using fitness-proportionate selection with a small mutation operator; and performing an iterative grid search to determine local maxima near each candidate.

14. The method of claim 1, further comprising:

generating, by the computing device and based on the registered VOIs of the imaged tissue, a visual indication of regions of the imaged tissue predicted to include cancer; and outputting, by the computing device, the visual indication of the predicted cancer.

15. The method of claim 14, wherein generating the visual indication of whether the imaged tissue is predicted to include cancer comprises generating an overlay image for the medical imaging data for the imaged tissue, the overlay including regions of the predicted cancer, and wherein outputting the indication comprises outputting, for display, the overlay image.

16. The method of claim 14, further comprising:

applying, by the computing device, a multiparametric model to generate a respective Composite Biomarker Score (CBS) for each voxel of the imaged tissue;

determining, by the computing device, locations of the CBS map that correspond to CBS values that satisfy a threshold; and generating the visual indication based on the CBS map.

17. The method of claim 16, wherein the multiparametric model specifies a multiparametric operation based on at least a first parameter and a second parameter that is based on co-registered histopathology data and respective sets of medical imaging training data.

18. The apparatus of claim 2, wherein the MM data comprises multiparametric magnetic resonance imaging (mpMRT) data .

19. The apparatus of claim 2, wherein the imaging series of MRI data is of a prostate.

20. The apparatus of claim 2 wherein the processor is further configured to:

capture the imaging series of MRI data using a combination of a surface array coil and an endorectal coil (ERC).

21. The apparatus of claim 2, wherein the processor is further configured to segment a prostate capsule on the imaging series.

22. The apparatus of claim 21, wherein to identify the VOI of the imaging series of MRI data, the processor is further configured to determine dimensions of the VOI based on the segmented prostate capsule.

23. The apparatus of claim 2, wherein the processor is further configured to correct distortions that affect the intensity values in each of the VOIs caused by signal inhomogeneities caused by the presence of the endorectal coil (ERC) in each of the VOIs.

24. The apparatus of claim 23, wherein to correct the distortions that affect the intensity values in each of the VOIs, the processor is further configured to:

model the ERC as two parallel wires perpendicular to the axial imaging plane of the imaged tissue;

calculate a differential contribution of each wire segment to the magnetic field in the xy- plane for each of the VOIs;

sum the differential contributions for each of VOIs to obtain a coil sensitivity profile for each of the VOIs;

register the sensitivity profile for each of the VOIs to the respective imaging series using a minimum variation metric as a similarity metric; and divide the intensity values of the imaging series by the respective registered coil sensitivity profile on a pixel-wise basis.

25. The apparatus of claim 2, wherein to compute the registration parameters for the VOIs, the processor is further configured to:

identify a target imaging series and a source imaging series from the prostate MM data; and determine an affine transformation to map points in each VOI in the images of the target imaging series to the source imaging series.

26. The apparatus of claim 25, wherein to determine registration parameters for the affine transformation the processor is further configured to:

apply the genetic algorithm to the VOIs to find candidates for the registration parameters, the genetic algorithm using fitness-proportionate selection with a small mutation operator; and perform an iterative grid search to determine local maxima near each candidate.

27. The apparatus of claim 2, wherein the processor is further configured to:

detect the presence of cancer in the registered VOIs; and output an indication of the detected cancer.

28. The apparatus of claim 2, wherein the apparatus comprises one of: (1) a medical imaging system, (2) a computer-aided design (CAD) system, and (3) a computing device.

29. The non-transitory computer-readable storage medium of claim 3, wherein the MRI data comprises multiparametric magnetic resonance imaging (mpMRI) data.

* * * * *

UNITED STATES PATENT AND TRADEMARK OFFICE

CERTIFICATE OF CORRECTION

PATENT NO. : 11,633,146 B2
APPLICATION NO. : 16/734139
DATED : April 25, 2023
INVENTOR(S) : Ethan Yize Leng, David Henry Porter and Gregory John Metzger It is certified that error appears in the above-identified patent and that said Letters Patent is hereby corrected as shown below:

In the Claims

Column 22, Claim 1, Line 52 reads: “imaging (MM) data” should read -- imaging (MRI) data --

Column 22, Claim 1, Line 55 reads: “series of the MM data” should read -- series of the MRI data --

Column 23, Claim 4, Line 39 reads: “imaging (MM) data” should read -- imaging (MRI) data --

Column 23, Claim 4, Line 42 reads: “series of the MM data” should read -- series of the MRI data --

Column 25, Claim 18, Line 18 reads: “wherein the MM data” should read -- wherein the MRI data --

Column 26, Claim 25, Line 17 reads: “the prostate MM data” should read -- the prostate MRI data --

Signed and Sealed this
Eighteenth Day of March, 2025

Coke Morgan Stewart
*Acting Director of the United States Patent and Trademark Office*